US009533035B2

(12) United States Patent
Zhang et al.

(10) Patent No.: US 9,533,035 B2
(45) Date of Patent: *Jan. 3, 2017

(54) TRUNCATED L1 PROTEIN OF HUMAN PAPILLOMAVIRUS TYPE 11

(75) Inventors: Jun Zhang, Xiamen (CN); Jin Wang, Xiamen (CN); Chunyan Yang, Xiamen (CN); Ying Gu, Xiamen (CN); Shaowei Li, Xiamen (CN); Ningshao Xia, Xiamen (CN)

(73) Assignees: XIAMEN UNIVERSITY, Siming District, Xiamen, Fujian Province (CN); BEIJING WANTAI BIOLOGICAL PHARMACY ENTERPRISE CO., LTD., Beijing (CN)

( * ) Notice: Subject to any disclaimer, the term of this patent is extended or adjusted under 35 U.S.C. 154(b) by 1213 days.

This patent is subject to a terminal disclaimer.

(21) Appl. No.: 12/601,983

(22) PCT Filed: May 29, 2008

(86) PCT No.: PCT/CN2008/001049
§ 371 (c)(1),
(2), (4) Date: Jan. 15, 2010

(87) PCT Pub. No.: WO2008/145020
PCT Pub. Date: Dec. 4, 2008

(65) Prior Publication Data
US 2010/0291141 A1 Nov. 18, 2010

(30) Foreign Application Priority Data
May 29, 2007 (CN) .......................... 2007 1 0105763

(51) Int. Cl.
*A61K 39/12* (2006.01)
*C07K 14/005* (2006.01)
*C12N 7/00* (2006.01)

(52) U.S. Cl.
CPC ............. *A61K 39/12* (2013.01); *C07K 14/005* (2013.01); *C12N 7/00* (2013.01); *C12N 2710/20022* (2013.01); *C12N 2710/20034* (2013.01)

(58) Field of Classification Search
None
See application file for complete search history.

(56) References Cited

U.S. PATENT DOCUMENTS

2002/0193565 A1* 12/2002 Stanley et al. ................ 530/350

FOREIGN PATENT DOCUMENTS

| CN | 1478790 | 3/2004 |
| CN | 1578787 | 2/2005 |
| CN | 1683010 | 10/2005 |
| CN | 101153280 | 4/2008 |
| WO | WO 94/20137 | 9/1994 |
| WO | WO 00/54730 | 9/2000 |
| WO | WO 03/078455 | 9/2003 |
| WO | WO 03/093437 A2 | 11/2003 |

OTHER PUBLICATIONS

Chen XS, Casini G, Harrison SC, Garcea RL. Papillomavirus capsid protein expression in *Escherichia coli*: purification and assembly of HPV11 and HPV16 L1. J Mol Biol. Mar. 16, 2001;307(1):173-82.*
Chen XS et al. Papillomavirus capsid protein expression in *Escherichia coli*: purification and assembly of HPV11 and HPV16 L1. J Mol Biol. Mar. 16, 2001;307(1):173-82.*
Villa LL et al. Immunologic responses following administration of a vaccine targeting human papillomavirus Types 6, 11, 16, and 18. Vaccine. Jul. 7, 2006;24(27-28):5571-83.*
Chen XS et al. Papillomavirus capsid protein expression in *Escherichia coli*: purification and assembly of HPV11 and HPV16 L1. J Mol Biol. Mar. 16, 2001;307(1)173-82.*
Villa LL et al. Immunologic responses following administration of a vaccine targeting human papillomavirus Types 6, 11, 16, and 18. Vaccine. Jul. 7, 2006;24(27-28):5571-83. Epub May 15, 2006.*
Li M et al. Expression of the human papillomavirus type 11 L1 capsid protein in *Escherichia coli*: characterization of protein domains involved in DNA binding and capsid assembly. J Virol. Apr. 1997;71(4):2988-95.*
GenBank: AAA46935.1. major capsid protein [Human papillomavirus type 11], Jun. 4, 1994. http://www.ncbi.nlm.nih.gov/protein/496201.*
GenBank: AAQ92369.1, HPV18 major capsid protein L1 [synthetic construct], Oct. 11, 2003 http://www.ncbi.nlm.nih.gov/protein/37528878?report=genbank&log$=protalign&blast_rank=1&RID=V8ACF90G015.*
Major capsid protein [Human papillomavirus type 6], GenBank: AAC80442.1, Apr. 13, 1999 http://www.ncbi.nlm.nih.gov/protein/3930543?report=genbank&log$=protalign&blast_rank=1&RID=V88RAMAW014.*
GenBank: AAC09292.1, late major capsid protein [Human papillomavirus type 16], Apr. 2, 1998 http://www.ncbi.nlm.nih.gov/protein/3005059?report=genbank&log$=protalign&blast_rank=4&RI.*
Fey et al. Demonstration of In Vitro Synthesis of Human Papilloma Viral Proteins from Hand and Foot Warts. J Invest Dermatol. 92:817-824, 1989.*
GenBank: AAC80442.1. major capsid protein [Human papillomavirus type 6]. Apr. 13, 1999.*
GenBank: AAC09292.1. late major capsid protein [Human papillomavirus type 16]. Apr. 2, 1998.*
Gen Bank: AAQ92369.1. HPV18 major capsid protein L1 [synthetic construct]. Dated Oct. 11, 2003.*
GenBank: AAA46935.1. major capsid protein [Human papillomavirus type 11]. Jun. 4, 1994.*
International Search Report.

(Continued)

*Primary Examiner* — Nick Zou
(74) *Attorney, Agent, or Firm* — Pillsbury Winthrop Shaw Pittman, LLP

(57) ABSTRACT

The invention relates to a truncated L1 protein of the Human Papillomavirus Type 11, a virus-like particle consisting of the protein, a vaccine comprising said virus-like particle, and the use of the vaccine in the prevention of condyloma acuminatum or HPV infections.

4 Claims, 6 Drawing Sheets

(56) References Cited

OTHER PUBLICATIONS

Zhuang, Min et al.; "Construction and Identification of Prokaryotic Expression System with L1 Gene of Human Papillomavirus Type 11" Chinese Journal of Endemiology, Mar. 20, 2004, vol. 23, No. 2, pp. 163-165, ISSN 1000-4955.

European Search Report corresponding to EP Application No. 08757380.4, dated Dec. 3, 2010.

Chen X, et al.: "Papillomavirus capsid protein expression in *Escherichia coli*: purification and assembly of HPV11 and HPV16 L1", Journal of Molecular Biology, vol. 301, No. 1, Mar. 16, 2001, pp. 173-182.

Rose, R.C., et al.: Expressionof human papillomavirus type 11 L1 protein in insect cells in-vivo and in-vitro assembly of viruslike particles, Journal of Virology, The American Society for Microbiology, vol. 67, No. 4, Apr. 1, 1993, pp. 1936-1944.

Bonnez, Willaim et al.: "Evolution of the antibody response to human papillomavirus type 11 (HPV-11) patients with condyloma acuminatum according to treatment response", Journal of Medical Vlrology, vol. 39, No. 4, 1993, pp. 340-344.

Xu, Xuemei et al.: "Transformation activity 1-6 and the immunogenicity of a human paillomavirus type 16 variant E6E7 gene from cervical carcinoma biopsy in Shangdong province", Xhnonqhua Weishenqwuxue He Mianvixue Zazhi, vol. 22, No. 4, Jul. 4, 2002.

Yan Chunyan et al.: "Expression, purification and immunogenicity of human papillomavirus type 11 virus-like particles from Excherichia coli", Weshengwu Xuebao, vol. 49, No. 11, Nov. 2009; pp. 1527-1533.

European Office Action for Appln. No. 08 757 380.4-1405 dated May 15, 2013.

European Office Action dated Oct. 20, 2014 for Appln. No. 08757380.4-1405.

Nygren P-A et al: "Engineering proteins to facilitate bioprocessing", Trends in Biotechnology, Elsevier Publications, Cambridge, GB, vol. 12, No. 5, May 1, 1994 (May 1, 1994), pp. 184-188, XP023594822, ISSN: 0167-7799, DOI: 10.1016/0167-7799(94)90080-9.

Murby M et al: "Hydrophobicity Engineering to Increase Solubility and Stability of a Recombinant Protein From Respiratory Syncytial Virus", European Journal of Biochemistry, Wiley-Blackwell Publishing Ltd, GB, vol. 230, No. 1, May 15, 1995 (May 15, 1995), pp. 38-44, XP000615209, ISSN: 00142956, DOI: 10.1111/J.1432-1033.1995.TB20531.X.

Schein Catherine H et al: "Deletions at the C-terminus of interferon gamma reduce RNA binding and activation of double-stranded-RNA cleavage by bovine seminal ribonuclease", Biochemical Journal, vol. 307, No. 1, 1995, pp. 123-127, XP055144242, ISSN: 0264-6021.

M. A. Dwyer: "Computational Design of a Biologically Active Enzyme", Science, vol. 304, No. 5679, Jun. 25, 2004 (Jun. 25, 2004), pp. 1967-1971, XP55144235, ISSN: 0036-8075, DOI: 10.1126/science.1098432.

R. Sterner: "Biochemistry: De Novo Design of an Enzyme", Science, vol. 304, No. 5679, Jun. 25, 2004 (Jun. 25, 2004), pp. 1916-1917, XP55144236, ISSN: 0036-8075, DOI: 10.1126/science.1100482.

European Search Report dated Jul. 27, 2015 for Appln. No. 15160363.6.

European Search Report dated Jul. 22, 2015 for Appln. No. 15160399.0.

Casini et al., "In vitro papillomavirus capsid assembly analyzed by light scattering", Virology vol. 325; No. 2, Aug. 1, 2004; pp. 320-327.

Indian Office Action dated Jul. 27, 2015 for Appln. No. 8058/DELNP/2009.

Neeper et al., "Expression of the major capsid protein of human papillomavirus type 11 in Saccharomyces cerevisae", Gene vol. 180, No. 1-2, Nov. 21, 1996; pp. 1-6.

Zhang et al., "Expression of human papillomavirus type 16 L1 protein in *Escherichia coli*: denaturation, renaturation, and self-assembly of virus-like particles in vitro". Virology, vol. 243, No. 2, Apr. 10, 1998; pp. 423-431.

Kelsall et al., "Expression of the major capsid protein of human papillomavirus type 16 in *Escherichia coli*", Journal of Virological Methods, vol. 53, No. 1, Jan. 1, 1995; pp. 75-90.

Chen et al., "Structure of small virus-like particles assembled from the L1 protein of human papillomavirus 16", Molecular Cell, vol. 5, No. 3, Mar. 1, 2000, pp. 557-567.

Li et al., "Expression of the human papillomavirus type 11 L1 capsid protein in *Escherichia coli*,: characterization of protein domains involved in DNA binding and capsid assembly"; Journal of virology, The American Society for Microbiology, vol. 71, Apr. 1, 1997; pp. 2988-2995.

Xu et al, "Papillomavirus virus-like particles as vehicles for the delivery of epitopes or genes", Archives of virology, vol. 151, No. 11, Jun. 22, 2006; pp. 2133-2148.

European Office Action dated Nov. 6, 2015 for Appln. No. 15160399.0.

* cited by examiner

1

2

3

1

2

3

TRUNCATED L1 PROTEIN OF HUMAN PAPILLOMAVIRUS TYPE 11

CROSS REFERENCE TO RELATED APPLICATIONS

This is the U.S. National Phase of PCT/CN2008/001049, filed May 29, 2008, which in turn claims priority to Chinese Patent Application No. 200710105763.2, filed May 29, 2007, the contents of both of which are incorporated herein in their entirety by reference.

FIELD OF THE INVENTION

The invention relates to a truncated L1 protein of the Human Papillomavirus Type 11, a virus-like particle consisting of the protein, a vaccine comprising said virus-like particle, and the use of the vaccine in the prevention of condyloma acuminatum and HPV (especially HPV11) infection.

BACKGROUND OF THE INVENTION

The human papillomavirus, a non-enveloped, deoxyribonucleic acid (DNA) virus, belongs to the genus of papovaviridae. The viral genome is a closed circle, double-stranded DNA, which is approximately 7.2-8 kb in length and contains 8 open reading frames (ORFs). The genome can be divided into three parts in terms of function: (1) the early region (E), approximately 4.5 Kb in length, coding for 6 non-structural proteins E1, E2, E4~E7 associated with virus replication, transcription and transformation; (2) the late region (L), approximately 2.5 Kb in length, coding for the major capsid protein L1 and the minor capsid protein L2; (3) the long control region (LCR), located between the end of the L region and the initiating terminal of the E region, approximately 800-900 bp in length, and comprising regulator elements for DNA replication and expression instead of coding for proteins. Viral particles are 45-55 nm in diameter, wherein the nucleocapsid, consisting of L1 and L2, exhibits icosahedral symmetry and comprise 72 capsomers.

Currently, there are over 90 different types of HPV, mainly causing papillary disease in the skin and mucosa of human. HPV types are divided into three groups depending on their relation with tumorigenesis: (1) group of low or no cancerogenic risk, containing types 6, 11, 39, 41, 42, and 43; (2) group of medium cancerogenic risk, containing types 31, 33, 35, 51, and 52; and (3) group of high cancerogenic risk, containing types 16, 18, 45, and 56.

Epidemiological investigation reveals that HPV (such as HPV6, 11) infection in the anal-genital mucosa is the third most common sexually transmitted disease following trichomoniasis and chlamydia. Pathological changes caused by HPV types 6 and 11 account for about 90% of these cases. In America, HPV infection of genital meatus among women occurs most frequently when they are 15-25 years old and is highly related to the infected person's sexual behavior. In China, HPV infection among women occurs most frequently when they are 20-29 years old, and the infection rate is 1606.1/100,000. Women are less infected with HPV as they grow older than 35. However, since the majority of HPV infections are sub-clinical, it is difficult to accurately estimate the infection rate. As estimated by the US CDC, the risk is approximately 10% during the whole life. In addition, there is little data regarding HPV infection among men, due to the difficulty of sample collection and the lesser severity of consequences. Currently, HPV infection rate among men is believed to be close to the one among women. In the United States, condyloma acuminatum can be found in 1% of sexually active adult men. Therefore, the development of a safe, efficient vaccine for HPV 6 and 11 would be an effective way to prevent sexually transmitted diseases.

HPV L1 protein, with a molecular weight of 55-60 kDa, is the major capsid protein of the human papillomavirus and the main target protein of the HPV vaccine. HPV L1 protein expressed in multiple different expression systems can form Virus-like particles (VLPs) which resemble native HPV particles morphologically, without the assistance of the L2 protein. The VLP, consisting of 72 pentamers of the L1 proteins, exhibits icosahedral symmetry. Since the VLPs retain the native epitopes of the viral particles, they are highly immunogenic and can induce the generation of neutralizing antibodies against homologous HPV (Kirnbauer, R., F. Booy, et al. 1992 Proc Natl Acad Sci USA 89(24): 12180-4). Furthermore, the VLPs are safe and have no potential cancergenic risk as they contain no viral DNA. Therefore, VLP vaccines become the primary candidate for an HPV vaccine.

The key for development of a vaccine is to efficiently produce VLP vaccines of HPV in large-scale. Currently, the most commonly used expression systems are eukaryotic expression systems and prokaryotic expression systems.

The commonly used eukaryotic systems comprise poxvirus, insect baculovirus and yeast vectors. HPV L1 protein expressed in eukaryotic systems shows little conformational difference from that of the native virus, and can self-assemble into VLPs. Thus, purified VLPs can be easily obtained after gradient density centrifugation. It brings a lot of convenience to the purification work. However, due to the high culture costs and low expression level, it is quite difficult to product industrially on a large-scale. The HPV vaccine Gardasil®, which came into the market recently, is more expensive than others due to low expression level and high production cost of the *Saccharomyces cerevisiae* expression system employed in its manufacture.

The expression of HPV L1 protein in a prokaryotic system such as *E. coli* has been previously reported. Banks, Matlashewski, et al. published a paper regarding the expression of HPV 16 L1 by employing *E. coli* (Banks, L., G. Matlashewski, et al. (1987). J Gen Virol 68 (Pt 12): 3081-9). However, most HPV L1 proteins expressed by *E. coli* lose their native conformation and cannot induce the generation of protective antibodies against HPV. Alternatively, although HPV VLPs can be obtained from the incorrectly folded proteins by steps such as purification from inclusion bodies and refolding, it is difficult to apply this method to large-scale production, as the protein is largely lost during the refolding process and the yield is low (Kelsall, S. R. and J. K. Kulski (1995). J Virol Methods 53(1): 75-90). Although HPV L1 protein may be expressed in a soluble form with a correct conformation in *E. coli* and dissolved in the supernatants of *E. coli* lysate, the expression level is low. Moreover, since there are large number and amount of impure proteins, it is difficult to isolate the proteins of interest from them. Although it is reported that the expression level of L1 protein can be increased in the supernatants by means of GST fusion expression and the purification of the protein of interest is facilitated (Li, M., T. P. Cripe, et al. (1997), J Virol 71(4): 2988-95), it still cannot be applied to large-scale production because expensive enzymes are required to cleave the fusion protein.

Therefore, a HPV L1 protein capable of inducing the generation of protective antibodies against HPV, and a virus-like particle consisting of the same are still needed in the art, so that it is possible to produce vaccines for condyloma acuminatum industrially on a large scale.

DESCRIPTION OF THE INVENTION

This invention aims to provide a novel HPV type 11 L1 protein, the virus-like particles (VLPs) consisting of it, and a vaccine comprising the VLPs.

During research, it was found by chance that the *E. coli* expression system can produce a truncated HPV 11 L1 protein that can induce the generation of neutralizing antibodies against HPV 11. After purification, the truncated HPV11 L1 protein can be produced in high yield, with at least 50% purity. Further treatment of the purified HPV L1 protein can produce VLPs, which can induce the production of neutralizing antibodies against HPV 11. The invention has been completed based on the above.

Therefore, the first aspect of the invention relates to HPV 11 L1 proteins with 3, 4, 5, or 6 amino acids truncated at N-terminal as compared to a wild type HPV 11 L1 protein. Preferably, the truncated protein has the sequence set forth in SEQ ID Nos:1, 2, 3, or 4, especially the sequence set forth in SEQ ID NO:1.

A further aspect of the invention relates to a polynucleotide encoding the truncated protein according to the invention, and a vector containing the polynucleotide.

A further aspect of the invention relates to a cell comprising the vector.

The invention also relates to a composition comprising the truncated protein, the polynucleotide, the vector, or the cell.

A further aspect of the invention relates to a HPV 11 VLP, comprising or consisting of a HPV 11 L1 protein with 3, 4, 5, or 6 amino acids truncated at the N terminal such as a HPV 11 L1 protein having a sequence set forth in SEQ ID NOs: 1, 2, 3, or 4.

A further aspect of the invention relates to a method for obtaining the HPV 11 L1 protein, comprising the expression of a truncated HPV 11 L1 gene fragment in an *E. coli* system and the subsequent purification of the protein from the lysate supernatant.

In a preferred embodiment of the invention, a method for obtaining HPV 11 L1 protein comprises:
  a) expressing the truncated HPV 11 L1 gene fragment in a *E. coli* expression system;
  b) disrupting *E. coli*, which has expressed the truncated HPV 11 L1 protein, in a salt solution at a concentration of from 100 mM to 600 mM, and isolating the supernatant;
  c) decreasing the salt concentration of the supernatant in b) to from 100 mM to 0, inclusive, by using water or a low salt solution, and collecting a precipitate;
  d) redissolving the precipitation in c) in a salt solution at a concentration of from 150 mM to 2500 mM, with a reductant added, and then isolating the resultant solution, wherein the solution contains the truncated HPV 11 L1 protein with a purity of at least 50%.

More generally, the invention also relates to a method for obtaining a HPV L1 protein, such as the HPV 11 L1 protein according to the invention, comprising:
  a) expressing a HPV L1 gene encoding the HPV L1 protein in an *E. coli* expression system;
  b) disrupting *E. coli*, which has expressed the HPV L1 protein, in a salt solution at a concentration of from 100 mM to 600 mM, and isolating the supernatant;
  c) decreasing the salt concentration of the supernatant in b) to from 100 mM to 0, inclusive, by using water or a low salt solution, and collecting a precipitate;
  d) redissolving the precipitation of c) in a salt solution at a concentration of from 150 mM to 2500 mM, with a reductant added, and then isolating the resultant solution, wherein the solution contains the HPV L1 protein with a purity of at least 50%.

The invention also relates to a vaccine for the prevention of condyloma acuminatum or HPV infection, comprising VLPs of HPV 11 L1 proteins according to the invention. Preferably, the vaccine further comprises at least one VLPs selected from VLPs of HPV18, 6, 16, 31, 33, 45, 52, and 58 L1 proteins. Generally, the vaccine further contains carriers or excipients useful for vaccine.

Preferably, the vaccine comprises HPV 6 VLPs and HPV 11 VLPs, especially the HPV 6 VLPs comprising or consisting of a protein having an amino acid sequence set forth in SEQ ID No: 7, and the HPV 11 VLPs comprising or consisting of a protein having an amino acid sequence set forth in SEQ ID No: 1. More preferably, the vaccine further comprises HPV 16 VLPs and HPV 18 VLPs, especially the HPV 16 VLPs comprising or consisting of a protein having an amino acid sequence set forth in SEQ ID No: 8, and the HPV 18 VLPs comprising or consisting of a protein having an amino acid sequence set forth in SEQ ID No: 9.

In a specially preferred embodiment, the vaccine comprises the HPV 6 VLPs comprising or consisting of a protein having an amino acid sequence set forth in SEQ ID No: 7, the HPV 11 VLPs comprising or consisting of a protein having an amino acid sequence set forth in SEQ ID No: 1, the HPV 16 VLPs comprising or consisting of a protein having an amino acid sequence set forth in SEQ ID No: 8, and the HPV 18 VLPs comprising or consisting of a protein having an amino acid sequence set forth in SEQ ID No: 9.

The invention further relates to the use of the HPV 11 L1 protein or the VLPs thereof in the manufacture of a vaccine for the prevention of condyloma acuminatum or HPV infections.

The invention further relates to a method for preventing condyloma acuminatum or HPV infections, comprising administrating a vaccine comprising an preventively effective amount of HPV 11 L1 protein to a human or animal in need of preventing condyloma acuminatum or HPV infections.

The invention involves a method for obtaining VLPs of the HPV 11 L1 protein, comprising:
  e) further purifying the truncated HPV 11 L1 protein with a purity of at least 50% by subjecting it to a chromatography;
  f) removing the reductant from the HPV 11 L1 protein obtained in e).

This invention involves a method for preparing a vaccine for preventing condyloma acuminatum or HPV infections, comprising blending the VLPs above, and optionally, one or more VLPs selected from the group consisting of VLPs of HPV 6, 16, 18, 31, 33, 45, 52 and 58, with carriers or excipients useful for vaccines.

DEFINITIONS OF THE TERM IN PRESENT INVENTION

According to the invention, the term "*E. coli* expression system" refers to a expression system consisting of *E. coli* (strains) and vectors, wherein the *E. coli* (strains) include, but are not limited to: GI698, ER2566, BL21 (DE3), B834 (DE3), and BLR (DE3), which are available on the market.

According to the invention, the term "vectors" refers to the nucleic acid carrier tools which can have a polynucleotide encoding a protein inserted therein and allow for the expression of the protein. The "vector" can have the carried genetic material expressed in a host cell by transformation, transduction, and transfection into the host cell. For example, "vectors" include plasmids, phages, cosmids and the like.

According to the invention, the term "a gene fragment of a truncated HPV 11 L1 protein" refers to the nucleic acids with the nucleotide(s) encoding one or more amino acid sequences deleted at 5' or 3' terminal of the wild-type HPV 11 L1 gene (cDNA). The full-length gene sequence of the wild-type HPV 11 L1 gene can be found in, but not limited to, the following NCBI sequences: M14119.1, AF335603.1 and AF335602.1.

The term "truncated HPV 11 L1 protein" refers to the protein with one or more amino acids deleted at the N- and/or C-terminal of the wild-type HPV 11 L1 protein. The full-length gene sequence of the wild-type HPV 11 L1 protein can be found in, but not limited to, the full-length L1 proteins encoded by the following NCBI sequences: M14119.1, AF335603.1 and AF335602.1.

According to the invention, the term "carriers or excipients useful for vaccines" refers to one or more reagents, including but not limited to: pH regulators, surfactants, adjuvants, and ionic strength enhancers. For example, pH regulators include, but are not limited to, phosphate buffers; surfactants include, but are not limited to: anion surfactants, cation surfactants, non-ionic surfactants (for example, but not limited to Tween-80); adjuvants include, but are not limited to, aluminum hydroxide and Freund's complete adjuvant; and Ionic strength enhancers include, but are not limited to, NaCl.

According to the invention, the term "chromatography" includes, but is not limited to: ion exchange chromatography (e.g. cation-exchange chromatography), hydrophobic interaction chromatography, absorbant chromatography (e.g. hydroxyapatite chromatography), gel filtrate chromatography (gel exclusion chromatography), and affinity chromatography.

According to the invention, the truncated HPV 11 L1 proteins may be obtained preferably by the following steps:
a) disrupting *E. coli*, which expresses truncated HPV 11 L1 protein, in a buffer containing 100-600 mM salt, preferably 200-500 mM;
b) isolating the supernatant from the disrupted solution, then decreasing the salt concentration of the supernatant to 100 mM-0M with water or a low-salt buffer (generally, with a salt concentration lower than the one of the buffer for disrupting);
c) separating a precipitant from the supernatant with a salt concentration as low as 100 mM-0;
d) redissoving the precipitant in a solution containing a reductant and having a salt concentration of 150-2000 mM, preferably greater than 200 mM;
e) isolating a solution of the truncated HPV 11 L1 proteins with a purity of at least 50%, preferably at least 70%, more preferably at least 80%.

According to the invention, in the method for obtaining the truncated HPV 11 L1 proteins, the term "buffer" refers to a solution which can maintain pH value stable within a certain range, including but not limited to: Tris buffers, phosphate buffers, HEPES buffers, and MOPS buffers.

According to the invention, the disrupting of the prokaryotic host cell may be achieved by methods including, but not limited to one or more of homogenizer disrupting, ultrasonic treatment, grinding, high pressure extrusion, and lysozyme treatment.

According to the invention, in the method for obtaining the truncated HPV 11 L1 proteins, the salts used include, but are not limited to: one or more of neutral salts, especially alkali metal salt, ammonium salts, hydrochlorides, sulfates, bicarbonates, phosphate salts or hydrogenphosphates, especially NaCl, KCl, $NH_4Cl$, $(NH_4)_2SO_4$. NaCl are preferred. The reductant used includes, but is not limited to, DTT and 2-mercaptoethanol, in an amount of including, but not limited to, 10-100 mM.

According to the invention, the VLPs of the truncated HPV 11 L1 protein may be produced by the following steps: further purifying the truncated HPV L1 protein with a purity of at least 50% by subjecting it to a chromatography, and thereby obtaining a purified truncated HPV 11 L1 protein solution; and removing the reductant from the purified HPV 11 L1 protein solution, and thereby obtaining the VLPs of the truncated HPV 11 L1. Methods for removing the reductant include, but are not limited to, known techniques in the art, such as dialysis, ultrafiltration, and chromatography.

According to the invention, the truncated HPV L1 protein preferably has the sequence set forth in SEQ ID NO:1.

According to the invention, the vaccine may be administrated in a patient-acceptable form, including but not limited to oral and injection, preferably injection.

According to the invention, the vaccine is preferably used in a unit dose. Each unit dose contains 5-80 μg truncated HPV 11 L1 VLP, preferably 20-40 μg.

BENEFICIAL EFFECT

Presently, the expression systems useful for preparing HPV VLPs include eukaryotic and prokaryotic expression systems.

HPV L1 proteins expressed in eukaryotic expression systems retain their native conformation, and can form VLPs on their own. In most cases, VLP with a correct conformation can be obtained by simple purification. Nevertheless, eukaryotic expression systems, such as the baculovirus and yeast expression systems, are difficult to be applied in large-scale industrial production due to low expression levels and high costs.

Prokaryotic expression systems, such as *E. coli* systems, have the advantages of high expression levels at a lower cost. However, when expressed in a prokaryotic system, the HPV L1 protein usually loses its native conformation and is expressed in a form of inclusion bodies in the precipitant. Renaturation of the protein from inclusion bodies is still a problem worldwide. Due to the difficulty and inefficiency of renaturation, this method is limited to small-scale lab research and cannot be applied on a large scale so as to obtain VLP with a correct conformation from the inclusive bodies. Although the HPV L1 protein can exist in its native conformation in the supernatant of *E. coli* lysate, its expression levels are low. Moreover, it is quite difficult to purify the HPV L1 protein from the numerous soluble proteins in the *E. coli* lysate supernatant. Generally, the purification is completed by means such as fusion expression and affinity chromatography which are not feasible for industrial-scale processes due to expensive enzymes employed therein.

In this invention, N-truncated HPV 11 L1 protein is expressed in an *E. coli* expression system and is selectively precipitated from the *E. coli* lysate supernatant under mild conditions. The HPV 11 L1 protein is then redissolved in a salt buffer to significantly improve its purity while still retaining its native conformation. The redissolved protein of interest can be immediately subjected to ion-exchange or hydrophobic interaction chromatography so as to obtain the pure protein. The purified, truncated HPV 11 L1 protein obtained from these steps, can self-assemble into VLPs with good immunogenicity and the ability to induce neutralizing antibodies of a high titer against HPV 11, which is a good vaccine for preventing human from HPV 11 infection. In addition, the truncated HPV 11 L1 protein used in the present invention, with the antigenicity and particle-selfassembly ability of the full-length HPV 11 L1 protein retained, is easily expressed in an *E. coli* expression system, and can be economically purified without using expensive enzymes. Furthermore, because the protein of interest is not subjected to the intensive procedures of denaturation and renaturation during purification, the method can be applied industrially on a large scale due to low loss.

The invention will be more apparent after referring to the detailed description and the drawings as follows. All public references are incorporated hereby by reference in their entirety.

SEQUENCES

Figure 1:
FIG. 1 shows the SDS-PAGE result of HPV11N4C-L1 protein during steps a)-d) of the method according to the invention. Lane 1: Lysate supernatant; Lane 2: HPV11N4C-L1 protein precipitated by tengenital flow; Lane 3: Redissolved HPV11N4C-L1 in a re-suspension solution. The result shows that the purity of HPV11N4C-L1 reached about 70% following the steps of precipitation and re-dissolution.

```
SEQ ID NO: 1:
  1 MSDSTVYVPP PNPVSKVVAT DAYVKRTNIF YHASSSRLLA VGHPYYSIKK
    VNKTVVPKVS

61 GYQYRVFKVV LPDPNKFALP DSSLFDPTTQ RLVWACTGLE VGRGQPLGVG
    VSGHPLLNKY

121 DDVENSGGYG GNPGQDNRVN VGMDYKQTQL CMVGCAPPLG EHWGKGTQCS
    NTSVQNGDCP
```

```
181  PLELITSVIQ  DGDMVDTGFG  AMNFADLQTN  KSDVPLDICG  TVCKYPDYLQ
     MAADPYGDRL

241  FFYLRKEQMF  ARHFFNRAGT  VGEPVPDDLL  VKGGNNRSSV  ASSIYVHTPS
     GSLVSSEAQL

301  FNKPYWLQKA  QGHNNGICWG  NHLFVTVVDT  TRSTNMTLCA  SVSKSATYTN
     SDYKEYMRHV

361  EEFDLQFIFQ  LCSITLSAEV  MAYIHTMNPS  VLEDWNFGLS  PPPNGTLEDT
     YRYVQSQAIT

421  CQKPTPEKEK  QDPYKDMSFW  EVNLKEKFSS  ELDQFPLGRK  FLLQSGYRGR
     TSARTGIKRP

481  AVSKPSTAPK  RKRTKTKK

SEQ ID NO: 2
  1  MPSDSTVYVP  PPNPVSKVVA  TDAYVKRTNI  FYHASSSRLL  AVGHPYYSIK
     KVNKTVVPKV

61  SGYQYRVFKV  VLPDPNKFAL  PDSSLFDPTT  QRLVWACTGL  EVGRGQPLGV
     GVSGHPLLNK

121  YDDVENSGGY  GGNPGQDNRV  NVGMDYKQTQ  LCMVGCAPPL  GEHWGKGTQC
     SNTSVQNGDC

181  PPLELITSVI  QDGDMVDTGF  GAMNFADLQT  NKSDVPLDIC  GTVCKYPDYL
     QMAADPYGDR

241  LFFYLRKEQM  FARHFFNRAG  TVGEPVPDDL  LVKGGNNRSS  VASSIYVHTP
     SGSLVSSEAQ

301  LFNKPYWLQK  AQGHNNGICW  GNHLFVTVVD  TTRSTNMTLC  ASVSKSATYT
     NSDYKEYMRH

361  VEEFDLQFIF  QLCSITLSAE  VMAYIHTMNP  SVLEDWNFGL  SPPPNGTLED
     TYRYVQSQAI

421  TCQKPTPEKE  KQDPYKDMSF  WEVNLKEKFS  SELDQFPLGR  KFLLQSGYRG
     RTSARTGIKR

481  PAVSKPSTAP  KRKRTKTKK

SEQ ID NO: 3
  1  MDSTVYVPPP  NPVSKVVATD  AYVKRTNIFY  HASSSRLLAV  GHPYYSIKKV
     NKTVVPKVSG

61  YQYRVFKVVL  PDPNKFALPD  SSLFDPTTQR  LVWACTGLEV  GRGQPLGVGV
     SGHPLLNKYD

121  DVENSGGYGG  NPGQDNRVNV  GMDYKQTQLC  MVGCAPPLGE  HWGKGTQCSN
     TSVQNGDCPP

181  LELITSVIQD  GDMVDTGFGA  MNFADLQTNK  SDVPLDICGT  VCKYPDYLQM
     AADPYGDRLF

241  FYLRKEQMFA  RHFFNRAGTV  GEPVPDDLLV  KGGNNRSSVA  SSIYVHTPSG
     SLVSSEAQLF

301  NKPYWLQKAQ  GHNNGICWGN  HLFVTVVDTT  RSTNMTLCAS  VSKSATYTNS
     DYKEYMRHVE

361  EFDLQFIFQL  CSITLSAEVM  AYIHTMNPSV  LEDWNFGLSP  PPNGTLEDTY
     RYVQSQAITC

421  QKPTPEKEKQ  DPYKDMSFWE  VNLKEKFSSE  LDQFPLGRKF  LLQSGYRGRT
     SARTGIKRPA

481  VSKPSTAPKR  KRTKTKK

SEQ ID NO: 4
  1  MSTVYVPPPN  PVSKVVATDA  YVKRTNIFYH  ASSSRLLAVG  HPYYSIKKVN
     KTVVPKVSGY

61  QYRVFKVVLP  DPNKFALPDS  SLFDPTTQRL  VWACTGLEVG  RGQPLGVGVS
     GHPLLNKYDD

121  VENSGGYGGN  PGQDNRVNVG  MDYKQTQLCM  VGCAPPLGEH  WGKGTQCSNT
     SVQNGDCPPL
```

```
181 ELITSVIQDG DMVDTGFGAM NFADLQTNKS DVPLDICGTV CKYPDYLQMA
    ADPYGDRLFF

241 YLRKEQMFAR HFFNRAGTVG EPVPDDLLVK GGNNRSSVAS SIYVHTPSGS
    LVSSEAQLFN

301 KPYWLQKAQG HNNGICWGNH LFVTVVDTTR STNMTLCASV SKSATYTNSD
    YKEYMRHVEE

361 FDLQFIFQLC SITLSAEVMA YIHTMNPSVL EDWNFGLSPP PNGTLEDTYR
    YVQSQAITCQ

421 KPTPEKEKQD PYKDMSFWEV NLKEKFSSEL DQFPLGRKFL LQSGYRGRTS
    ARTGIKRPAV

481 SKPSTAPKRK RTKTKK

SEQ ID NO: 5
   1 ATGTGGCGGC CTAGCGACAG CACAGTATAT GTGCCTCCTC CCAACCCTGT
     ATCCAAGGTT

61 GTTGCCACGG ATGCGTATGT TAAACGCACC AACATATTTT ATCACGCCAG
     CAGTTCTAGA

121 CTCCTTGCTG TGGGACATCC ATATTACTCT ATCAAAAAAG TTAACAAAAC
     AGTTGTACCA

181 AAGGTGTCTG GATATCAATA TAGAGTGTTT AAGGTAGTGT TGCCAGATCC
     TAACAAGTTT

241 GCATTACCTG ATTCATCTCT GTTTGACCCC ACTACACAGC GTTTAGTATG
     GGCGTGCACA

301 GGGTTGGAGG TAGGCAGGGG TCAACCTTTA GGCGTTGGTG TTAGTGGGCA
     TCCATTGCTA

361 AACAAATATG ATGATGTAGA AAATAGTGGT GGGTATGGTG GTAATCCTGG
     TCAGGATAAT

421 AGGGTTAATG TAGGTATGGA TTATAAACAA ACCCAGCTAT GTATGGTGGG
     CTGTGCTCCA

481 CCGTTAGGTG AACATTGGGG TAAGGGTACA CAATGTTCAA ATACCTCTGT
     ACAAAATGGT

541 GACTGCCCCC CGTTGGAACT TATTACCAGT GTTATACAGG ATGGGACAT
     GGTTGATACA

601 GGCTTTGGTG CTATGAATTT TGCAGACTTA CAAACCAATA AATCGGATGT
     TCCCCTTGAT

661 ATTTGTGGAA CTGTCTGCAA ATATCCTGAT TATTTGCAAA TGGCAGCAGA
     CCCTTATGGT

721 GATAGGTTGT TTTTTTATTT GCGAAAGGAA CAAATGTTTG CTAGACACTT
     TTTTAATAGG

781 GCCGGTACTG TGGGGGAACC TGTGCCTGAT GACCTGTTGG TAAAAGGGGG
     TAATAATAGA

841 TCATCTGTAG CTAGTAGTAT TTATGTACAT ACACCTAGTG GCTCATTGGT
     GTCTTCAGAG

901 GCTCAATTAT TTAATAAACC ATATTGGCTT CAAAAGGCTC AGGGACATAA
     CAATGGTATT

961 TGCTGGGGAA ACCACTTGTT TGTTACTGTG GTAGATACCA CACGCAGTAC
     AAATATGACA

1021 CTATGTGCAT CTGTGTCTAA ATCTGCTACA TACACTAATT CAGATTATAA
     GGAATACATG

1081 CGCCATGTGG AAGAGTTTGA TTTACAGTTT ATTTTTCAAT TGTGTAGCAT
     TACATTATCT

1141 GCAGAAGTCA TGGCCTATAT ACACACAATG AATCCTTCTG TTTTGGAGGA
     CTGGAACTTT

1201 GGTTTATCGC CTCCACCAAA TGGTACACTG GAGGATACTT ATAGATATGT
     ACAGTCACAG
```

-continued

```
1261  GCCATTACCT GTCAGAAACC CACACCCGAA AAAGAAAAAC AGGACCCCTA
      TAAGGATATG

1321  AGTTTTTGGG AGGTTAACTT AAAAGAAAAG TTTTCTTATG AATTAGATCA
      GTTTCCCCTT

1381  GGACGTAAGT TTTTATTGCA AAGTGGATAT CGAGGACGGA CGTCTGCTCG
      TACAGGTATA

1441  AAGCGCCCAG CTGTGTCTAA GCCCTCTACA GCCCCCAAAC GAAAACGTAC
      CAAAACCAGA

1501  AAGTAA

SEQ ID NO: 6
   1  ATGAGCGACA GCACAGTATA TGTGCCTCCT CCCAACCCTG TATCCAAGGT
      TGTTGCCACG

61  GATGCGTATG TTAAACGCAC CAACATATTT TATCACGCCA GCAGTTCTAG
      ACTCCTTGCT

121  GTGGGACATC CATATTACTC TATCAAAAAA GTTAACAAAA CAGTTGTACC
      AAAGGTGTCT

181  GGATATCAAT ATAGAGTGTT TAAGGTAGTG TTGCCAGATC CTAACAAGTT
      TGCATTACCT

241  GATTCATCTC TGTTTGACCC CACTACACAG CGTTTAGTAT GGGCGTGCAC
      AGGGTTGGAG

301  GTAGGCAGGG GTCAACCTTT AGGCGTTGGT GTTAGTGGGC ATCCATTGCT
      AAACAAATAT

361  GATGATGTAG AAAATAGTGG TGGGTATGGT GGTAATCCTG GTCAGGATAA
      TAGGGTTAAT

421  GTAGGTATGG ATTATAAACA AACCCAGCTA TGTATGGTGG GCTGTGCTCC
      ACCGTTAGGT

481  GAACATTGGG GTAAGGGTAC ACAATGTTCA ATACCTCTG TACAAAATGG
      TGACTGCCCC

541  CCGTTGGAAC TTATTACCAG TGTTATACAG GATGGGGACA TGGTTGATAC
      AGGCTTTGGT

601  GCTATGAATT TTGCAGACTT ACAAACCAAT AAATCGGATG TTCCCCTTGA
      TATTTGTGGA

661  ACTGTCTGCA AATATCCTGA TTATTTGCAA ATGGCAGCAG ACCCTTATGG
      TGATAGGTTG

721  TTTTTTTATT TGCGAAAGGA ACAAATGTTT GCTAGACACT TTTTTAATAG
      GGCCGGTACT

781  GTGGGGGAAC CTGTGCCTGA TGACCTGTTG GTAAAAGGGG GTAATAATAG
      ATCATCTGTA

841  GCTAGTAGTA TTTATGTACA TACACCTAGT GGCTCATTGG TGTCTTCAGA
      GGCTCAATTA

901  TTTAATAAAC CATATTGGCT TCAAAAGGCT CAGGGACATA ACAATGGTAT
      TTGCTGGGGA

961  AACCACTTGT TTGTTACTGT GGTAGATACC ACACGCAGTA CAAATATGAC
      ACTATGTGCA

1021  TCTGTGTCTA AATCTGCTAC ATACACTAAT TCAGATTATA AGGAATACAT
      GCGCCATGTG

1081  GAAGAGTTTG ATTTACAGTT TATTTTTCAA TTGTGTAGCA TTACATTATC
      TGCAGAAGTC

1141  ATGGCCTATA TACACACAAT GAATCCTTCT GTTTTGGAGG ACTGGAACTT
      TGGTTTATCG

1201  CCTCCACCAA ATGGTACACT GGAGGATACT TATAGATATG TACAGTCACA
      GGCCATTACC

1261  TGTCAGAAAC CCACACCCGA AAAGAAAAA CAGGACCCCT ATAAGGATAT
      GAGTTTTTGG
```

```
1321 GAGGTTAACT TAAAAGAAAA GTTTTCTTAT GAATTAGATC AGTTTCCCCT
     TGGACGTAAG

1381 TTTTTATTGC AAAGTGGATA TCGAGGACGG ACGTCTGCTC GTACAGGTAT
     AAAGCGCCCA

1441 GCTGTGTCTA AGCCCTCTAC AGCCCCCAAA CGAAAACGTA CCAAAACCAG
     AAAGTAA
```

The description is further illustrated in combination with the Examples, wherein it is not limited to the Examples.

EXAMPLE 1

Expression of the Truncated HPV11 L1 Protein (SEQ ID NO.1)

Preparation of HPV11 L1 Gene Fragments as PCR Template

The full-length gene of HPV-11 L1 was synthesized by Shanghai Boya Bio Co. The synthesized gene fragment has a full length of 1506 by and has a sequence of SEQ ID NO:5. Based on the synthetic full-length gene fragment of HPV-11 L1, the truncated HPV 11 L1 protein according to the invention was prepared as a template.

Construction of Non-Fusion Expression Vector of Truncated HPV11 L1 Gene

The full-length gene fragment of HPV-11 L1 synthesized in the previous step were used as the template for the next PCR reaction. The forward primer was 11N4F: 5'-CATATG AGC GAC AGC ACA GTA TAT GTG-3' (SEQ ID NO: 10), at the 5' terminal of which the restriction endonuclease NdeI site was introduced. The sequence of NdeI site was CAT ATG, wherein ATG was the initiation codon in *E. coli* system. The reverse primer was 6CR: 5'-GTCGAC TTA CTT TCT GGT TTT GGT ACG TTT-3' (SEQ ID NO: 11), at the 5' terminal of which the restriction endonuclease SalI site was introduced. Amplification was performed in a Biometra T3 PCR thermocycler using the following parameters:

| | |
|---|---|
| 94° C. denaturation 5 min | 1 cycle |
| 94° C. denaturation 50 sec | 25 cycles |
| 57° C. annealing 50 sec | |
| 72° C. elongation 2 min | |
| 72° C. elongation 10 min | 1 cycle |

The DNA fragments, about 1.5 kb in length, were obtained after amplification. The PCR products were linked to the pMD 18-T vector (Takara Biosciences). After digestion with NdeI/SalI, it was identified that positive colonies, wherein the truncated HPV11 L1 gene was inserted, were obtained, designated as pMD 18-T-HPV11N4C-L1.

The nucleotide sequence of interest, which was inserted into the plasmid pMD 18-T-HPV11N4C-L1, was determined as SEQ ID NO: 6 by Shanghai Boya Bio Co. through using M13+/– primers. SEQ ID NO:6 encodes the amino acid sequence set forth in SEQ ID NO:1 which corresponds to a HPV 11 L1 protein having 4 amino acids truncated at its N-terminal and no amino acid truncated at its C-terminal and was designated as HPV11N4C-L1.

The truncated HPV11N4C-L1 gene fragments were obtained by NdeI/SalI digestion of plasmid pMD 18-T-HPV11N4C-L1. The fragments were linked to Non-Fusion Expression Vector pTO-T7 (Luo Wenxin et al., Chinese Journal of Biotechnology, 2000, 16:53-57). Colonies were screened with NdeI/SalI digestion. Positive colonies containing the insert of the L1 gene fragment were labeled pTO-T7-HPV11N4C-L1. 1 μL plasmid pTO-T7-HPV11N4C-L1 (0.15 mg/ml) was used to transform 40 μL competent *E. coli* ER2566 (New England Labs) prepared by Calcium chloride method, and then was coated on solid LB medium containing kanmycin (at a final concentration of 25 mg/mL, the same as below). The plates were incubated at 37° C. for about 10-12 h until single colonies could be observed clearly. Single colonies were transferred to a tube containing 4 ml liquid LB medium containing kanmycin. Cultures were incubated in a shaking incubator at 220 rpm for 10 h at 37° C., and then 1 ml bacterial solution was freeze-dried and stored at −70° C.

Expression of HPV11N4C-L1 in Large Scale

*E. coli* transformed with pTO-T7-HPV11N4C-L1 was taken from the freeze-dried strain at −70° C. and diluted with a little sterile water, and then incubated in 50 mL LB medium containing Kanamycin at 200 rpm and 37° C. for 8 h. Then, the cultures were transferred to ten flasks (5 ml culture per flask), each of which contains 500 mL LB medium, and were incubated in a shaking incubator overnight at 200 rpm and 30° C. The cultures were the starter cultures.

LB medium:
Peptone: 10 g
Yeast extract: 5 g
NaCl: 10 g

The above components were dissolved in 1 L deionized water; the resultant solution was adjusted to pH 7.2 by addition of NaOH, sterilized at 121° C. for 30 minutes and cooled to 50° C.

A 50 L fermenter made by Shanghai Baoxing Biological Ltd was used in large-scale incubation. pH electrode was calibrated. 30 L LB medium was prepared and transferred into the fermenter, sterilized in situ at 121° C. for 30 minutes. Dissolved oxygen electrode was calibrated, wherein the value was determined as 0 before introduction of air after sterilization and as 100% prior to vaccination after introduction of air while stirring at 100 rpm at the beginning.

Preparation of the feed: 20 g peptone and 10 g yeast extract were dissolved in 100 ml deionized water to prepare a mixture of peptone and yeast extract (30%), and 50 g glucose was dissolved in 100 ml deionized water to prepared a glucose solution (50%). The two mixtures were sterilized at 121° C. for 20 min.

On the second day, the starter cultures in the ten flasks (for a total of 5 L) were transferred to the fermenter. At 37° C. and pH 7.0, the dissolved $O_2$ was maintained at >40% by regulating agitation rate or air supply manually.

Flow Feed: 50% glucose and 30% mixture of peptone and yeast extract were mixed at a 2:1 mass ratio.

Flow rates were as follows:
25 mL/min was defined as 100%.
1 h: 5%
2 h: 10%
3 h: 20%

4 h: 40%

5 h to the end: 60%

When $OD_{600nm}$ reached about 10, the culture temperature was lowered to 25° C. and 4 g IPTG was added to begin induction culture of 4 h. Fermentation was halted when $OD_{600nm}$ reached about 60. The culture was then centrifuged to obtain target strains expressing the HPV11N4C-L1 protein (about 2.7 kg).

EXAMPLE 2

Preparation HPV11N4C-L1 with a purity of about 70%

1 g strains were re-suspended in 10 ml lysis buffer (20 mM tris buffer pH 7.2, 300 mM NaCl). Strains were disrupted by passing through a APV homogenizer (Invensys Group) for five times at a pressure of 600 bar. The homogenate was centrifuged at 30,000 g (13,500 rpm in JA-14 rotor) for 15 min. The supernatant was subjected to SDS-PAGE on a 10% gel. At this stage, the HPV11N4C-L1 had a purity of about 10%. The supernatant was dialyzed by a Centrasette 5 Tangential Flow Filter (Pall Co.) running at a pressure of 0.5 psi, a flow rate of 500 ml/min, and a tangential flow rate of 200 mL/min, wherein the retention molecular weight was 30 kDa, the dialysate was 10 mM phosphate buffer pH 6.0, and the dialysis volume was three times as large as the volume of supernatant. After thorough dialysis, the mixture was centrifuged at 12,000 g (9500 rpm in JA-10 rotor (Beckman J25 high speed centrifuge)) for 20 min, and the precipitation was collected. The precipitation was re-suspended in 10 mM phosphate buffer pH 8.0 containing 10 mM DTT and 300 mM NaCl, wherein the volume of the buffer was 1/10 times as large as the volume of the supernatant. The mixture was stirred for 30 min and centrifuged at 30,000 g (13,500 rpm in JA-14 rotor (Beckman J25 high speed centrifuge)) for 20 min. The supernatant passes through a 0.22 μm filter membrane. The sample was further subjected to cation exchange chromatography. 30 μL of 6× loading buffer was added to 150 μL of the filtered supernatant, and the result solution was mixed. After heating in a water bath at 80° C. for 10 min, a 10 uL sample was subjected to SDS-PAGE on a 10% gel at 120V for 120 min. The electrophoretic bands were stained by Coomassie brilliant blue. The result was shown in FIG. 1. According to the analysis of SDS-PAGE, HPV11N4C-L1 protein was purified and enriched after the steps of precipitation and re-dissolution, with the purity increased to about 70%.

EXAMPLE 3

Chromatography Purification of HPV11N4C-L1

Cation Exchange Chromatography of HPV11N4C-L1
Equipment: AKTA Explorer 100 preparative liquid chromatography system (GE Healthcare, i.e. the original Amershan Pharmacia Co.)
Chromatographic media: SP Sepharose 4 Fast Flow
Column Volume: 5.5 cm×20 cm
Buffer: 20 mM phosphate buffer pH 8.0, 10 mM DTT
20 mM phosphate buffer pH 8.0, 10 mM DTT, 2M NaCl
Flow Rate: 25 mL/min
Detector Wavelength: 280 nm
Sample: 3 L, about 70% HPV11N4C-L1 solution
Elution protocol: eluting undesired proteins with 200 mM NaCl, eluting the protein of interest with 800 mM NaCl, collecting 500 mM NaCl elutate, and finally getting about 700 mL purified HPV11N4C-L1 sample.

Purification of HPV11N4C-L1 by CHT-II Chromatography
Equipment: AKTA Explorer 100 preparative liquid chromatography system (GE Healthcare, i.e. the original Amershan Pharmacia Co.)
Chromatographic media: CHT-II (Bio-Rad)
Column Volume: 5.5 cm×20 cm
Buffer: 10 mM phosphate buffer pH7.0, 10 mM DTT, 0.5M NaCl
Flow Rate: 20 mL/min
Detector Wavelength: 280 nm
Sample: 500 mM NaCl elutate from SP Sepharose 4 Fast Flow
Elution protocol: directly collecting the pass-through containing the protein of interest.

Figure 2:
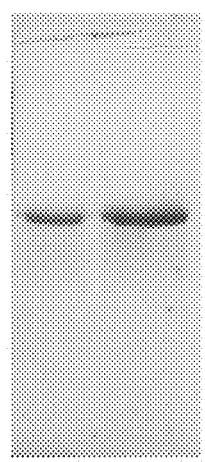
FIG. 2 shows the SDS-PAGE result of HPV11N4C-L1 that was obtained in step d) and was further purified according to step e). Lane 1: HPV11N4C-L1 purified according to step e), 10 μL; Lane 2: HPV11N4C-L1 purified according to step e), 20 μL. The result shows that HPV11N4C-L1 purified according to step e) reached a purity of about 98%.

The pass-through, which contains HPV11N4C-L1, was collected and about 300 mL purified HPV11N4C-L1 was obtained. 30 μL 6× loading buffer was added to 150 μL HPV11N4C-L1 sample purified according to the method of the Example, and then the result solution was mixed thoroughly. After heating the solution in a water bath at 80° C. for 10 min, a 10 uL sample was subjected to SDS-PAGE on a 10% gel at 120V for 120 min. The electrophoretic bands were stained by Coomassie brilliant blue. The result was shown in FIG. 2. The concentration of the protein of interest was about 0.3 mg/ml, and the purity was greater than 98% according to SDS-PAGE.

EXAMPLE 4

Assembly of HPV11N4C-L1 VLPs

Equipment: Centrasette 5 Tangential Flow Filter (Pall Co.), retention MW 30 kDa.
Sample: 300 mL HPV11N4C-L1 obtained in Example 3
Sample Concentration Sample was concentrated to 800 mL with the system tangential flow rate adjusted to 50 mL/min
Sample Renaturation: Sample buffer was exchanged with 10 L renaturation buffer (20 mM PB pH 6.0, 2 mM $CaCl_2$, 2 mM $MgCl_2$, 0.5M NaCl, 0.003% Tween-80) thoroughly. When running the Tangential Flow Filter, the pressure was 0.5 psi and the tangential flow rate was 10 mL/min. When exchange was finished, the sample buffer was replaced with storage buffer (20 L PBS: 20 mM PB pH 6.5, 0.5M NaCl). The exchange volume was 20 L. The running pressure was 0.5 psi and the tangential flow rate was 25 mL/min. When the liquid exchange was finished, the sample was aseptically filtrated with a Pall filter (0.20 μm). The HPV11N4C-L1 VLPs were obtained and were stored at for further use.

EXAMPLE 5

Determination of the Morphology of HPV11N4C-L1 VLPs

Figure 3:
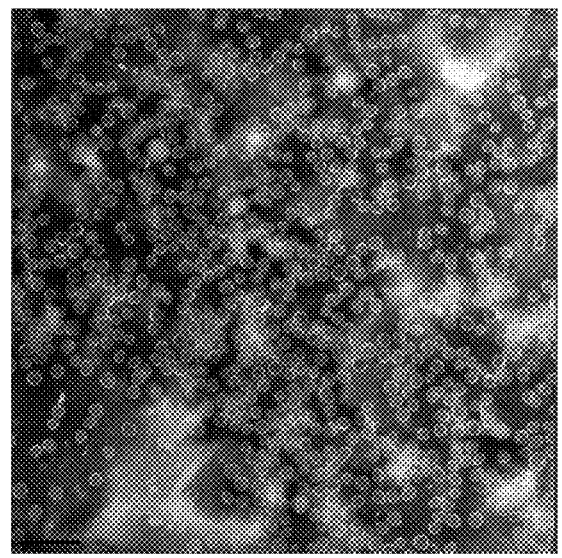
FIG. 3 shows the transmission electron microscopy (TEM) photograph of HPV11N4C-L1 VLPs obtained in step f), taken at 50,000× magnification. A great deal of VLPs in a radius of about 25 nm were observed in visual field, wherein the particle size was consistant with the theoretic size and the particles were homogenous.

Transmission Electron Microscopy (TEM) of HPV11N4C-L1 VLPs
The equipment was a JEOL 100 kV Transmission Electron Microscope (100,000× magnification). HPV11N4C-L1 VLPs were negatively stained with 2% phosphotungstic acid at pH 7.0, and fixed on a copper grid. Results were shown in FIG. 3. It could be seen that the VLPs obtained in Example 4 had a radius of approximately 25 nm, and were homogenous and in a hollow form.

Dynamic Light-Scattering Measurement of HPV11N4C-L1 VLPs

Figure 4:
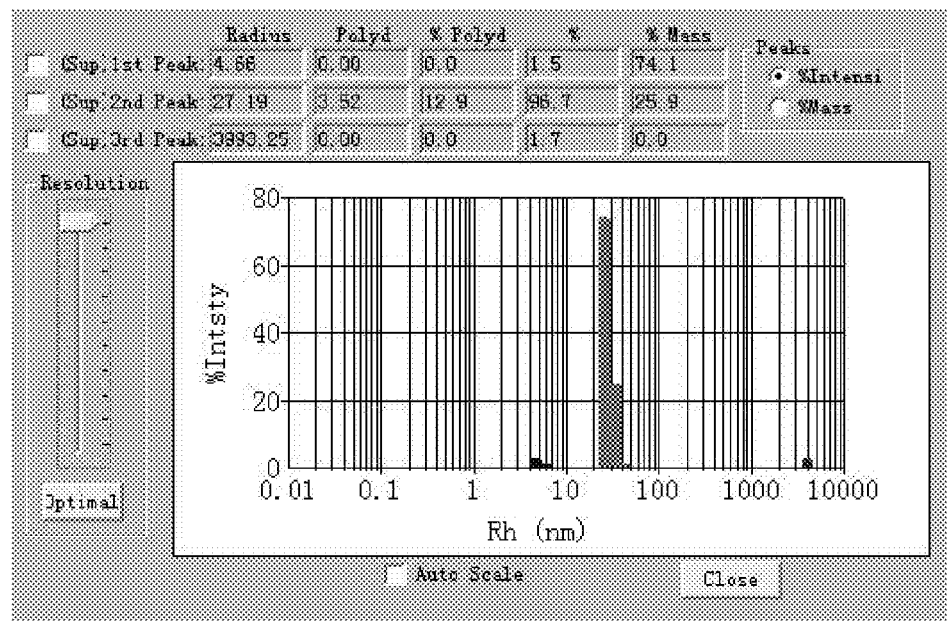
FIG. 4 shows the dynamic light-scattering measurement result of HPV11N4C-L1 VLPs obtained in step f). The result shows that HPV11N4C-L1 VLP had a hydrodynamic radius of 27.19 nm and a particle assembly rate of 96.7%.

DynaPro MS/X dynamic light-scattering instrument (including a temperature controller) (US Protein Solutions Co.) was used for light-scattering measurements. The regulation algorithm was used in the measurements. The sample was the one obtained in Example 4. The sample was passed through a 0.22 μm filter membrane prior to the measurement. Results were shown in FIG. 4. The result shows that HPV11N4C-L1 VLPs had a Hydrodynamic radius of 27.19 nm and a particle assembly rate of 96.7%.

Establishment of Pseudovirion Neutralization Assay for HPV11

HPV can hardly be cultured in vitro, and the HPV host had a strong specificity. Thus, HPV can hardly be propagated in hosts other than human. That is, there was not an appropriate animal model for HPV. Therefore, in order to evaluate the immune productivity of HPV vaccine quickly, there was a need to establish a efficient model for in vitro neutralization assays.

In Vitro Infection Model of Pseudovirion: According to the characteristic that HPV VLP can package nucleic acids non-specifically, HPV pseudivirion was formed by expressing HPV L1 and L2 protein in cells, and by packaging viral DNA of episome or introducing reporter plasmids heterologously. Methods include expression systems based on recombinant viruses and cotransfection of multi-plasmids (see Yeager, M. D, Aste-Amezaga, M. et al (2000) Virology (278) 570-7).

The invention utilizes cotransfection of a multi-plasmid system. Some improvements were made as follows. An optimized calcium phosphate transfection method was established for the 293FT cell line, with a transfection efficiency of above 90%, which facilitate the production on a large scale. The resultant codon-optimized expression plasmid of HPV structural protein could express HPV L1 and L2 gene efficiently in mammalian cell lines, facilitating efficient assembly of pseudovirion.

Construction of HPV Pseudovirion:

P11L1h, p11L2h and pN31-EGFP (donated by Professor John T. Schiller of NIH) contain genes for HPV11L1, HPV11L2, and GFP, respectively. These plasmids were purified using CsCl density gradient centrifugation as described in The Molecular Cloning Experiment Guide, (3rd edition). The purification procedure was as follows:

Plasmids were used to transform *E. coli* DH5α;

Single colonies were transferred into 500 mL LB culture medium and incubated in a shaking flask at 37° C. for 16 h;

Culture medium was centrifuged at 9,000 g for 5 min and the stains were collected;

The following substances were successively added to bacteria in each 1000 mL LB: 40 mL solution I (50 mM glucose, 25 mM Tris-Cl pH 8.0, 10 mM EDTA pH 8.0) and 2 ml 1 μg/μL RNase A), 40 mL solution II (0.2M NaOH, 1% SDS), and 48 mL solution III (60.0 mL 5M potassium acetate, 11.5 mL acetic acid, and 28.5 mL deionized water);

After placing on ice for 10 min, the mixture was centrifuged at 15,000 g for 20 min at 4° C.;

The supernatant was mixed with 0.6 volume of isopropyl alcohol, then was centrifuged again at 15,000 g for 30 min at 4° C.;

The supernatant was decanted into waste and the precipitation was washed with 70% ethanol;

The precipitation was dissolved in TE and the content of DNA was determined;

CsCl was dissolved in the solution of DNA (1 g DNA per 1.01 g CsCl), and then 100 μL 10 mg/mL EB solution was also dissolved in it;

The mixture was centrifuged using a Beckman NVT65 centrifuge at 62,000 rpm for 10 hr at 20° C.;

Closed circle DNA section was collected using an injector pinhead;

EB was extracted with equivalent volume of Isoamyl alcohol repeatedly for four times;

Three volumes of deionized water and eight volumes of dry ethanol were added to one volume of DNA solution, and then the mixture was centrifuged at 20000 g for 30 min at 4° C.;

The DNA precipitation was collected and washed with 75% ethanol, and then dissolved in 1 mL TE;

The concentration of the DNA solution was determined, then the solution was stored in small packages at −20° C.

The purified p11L1h, p11L2h and pN31-EGFP co-transfected 293FT cells (Invitrogen) cultured on a 10 cm cell culture plate by calcium phosphate method. The calcium phosphate method was described as follows. 40 μg p11L1h, 40 μg p11L2h, and 40 μg pN31-EGFP were separately added to the mixture of 1 mL HEPES solution (125 μL 1M HEPES/50 mL deionized water, at pH7.3 and 4° C.) and 1 mL 0.5M $CaCl_2$ solution. After mixing, 2 mL 2× HeBS solution (0.28M NaCl (16.36 g), 0.05M HEPES (11.9 g), 1.5 mM $Na_2HPO_4$ (0.213 g), dissolved in 1000 mL deionized water, at pH 6.96 and −70° C.) was added dropwise. After standing at room temperature for 1 min, the mixture was added to the 10 cm cell culture plate where the 293FT cells were cultured. The original culture medium was replaced with 10 ml complete medium (Invitrogen Co.) 6 hours later. 48 hours after transfection, the medium was decanted and the cells were washed twice with PBS. Then, the cells were collected and counted. Every $10^8$ cells were suspended in 1 mL cytolytic solution (0.25% Brij58, 9.5 mM $MgCl_2$). After lysing, cell lysate was centrifugated at 5,000 g for 10 min and the supernatant was collected. The Pseudovirion solution was obtained after adding 5M NaCl to the supernatant to a final concentration of 850 mM, then was stored in small packages at −20° C.

293FT cells (Invitrogen) were spread on a 96-well cell culture plate ($1.5 \times 10^4$ cells/well). Neutralization assay was performed five hours later. Serum samples were serially diluted with 10% DMEM half-by-half 50 μL diluted samples were separately mixed with 50 μL Pseudovirion solutions diluted with 10% DMEM (moi=0.1). After incubating at 4° C. for 1 h, the mixture was added to the 96-well cell culture plate spread with 293FT cells. The mixture was then incubated for 72 h at 37° C. Neutralization titers of samples were estimated by observing fluorescence. Infection percentage of cells in each well was checked by flow cytometry (EPICS XL, American Beckman Coulter Co.). The exact titers of monoclonal antibodies or polyclonal antibodies were calculated. Infection percentage was the percentage of cells in the positive region minus the uninfected cells in the positive region.

Infection control percentage=(1−infection percentage of sample cell/infection percentage of negative cell)×100%

Neutralization titer was defined as the highest dilution multiple by which the infection control percentage was just above 50%. Monoclonal and polyclonal antibodies were considered as having neutralizing capacity if their infection control percentage was above 50% after 50 times dilutions.

Measurement of Immune Protection of Animals Vaccinated with HPV11 VLPs:

Female rabbits (general level), 6-8 weeks old, were purchased from the Disease Prevention and Control Center of Guangxi province, where they were raised. HPV11N4C-L1 VLPs prepared in Example 4, were mixed with equal amount of complete Freund's Adjuvant for the first immunization. For the booster, HPV11N4C-L1 VLPs were mixed with incomplete Freund's Adjuvant. Rabbits were immunized via muscle injection, with 100 μg per rabbit for the first immunization, and with 50 μg per rabbit for the booster separately at week 4, 10. After immunization, external vein blood was collected every week, and serum was separated and stored for detection.

Figure 5:
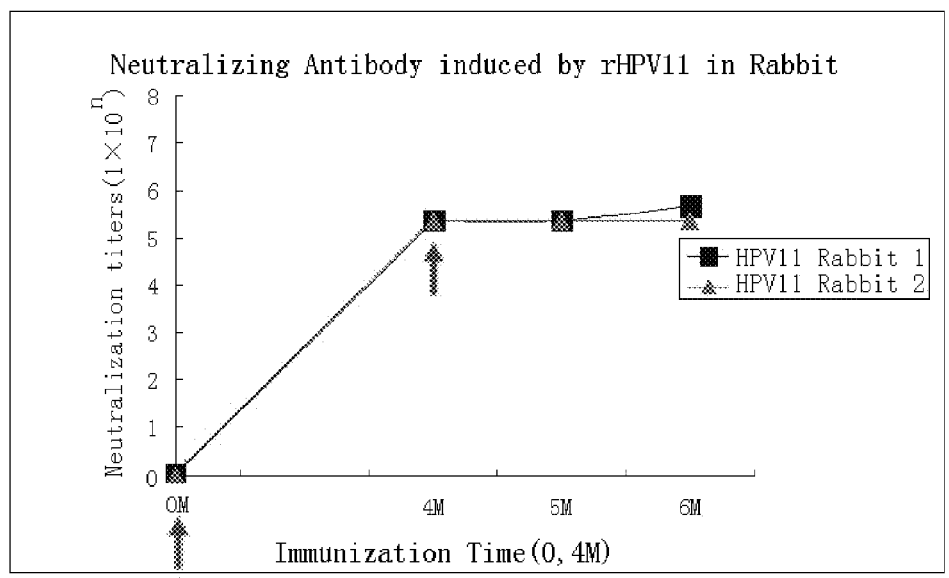
FIG. 5 shows titers of neutralizing antibodies in serum at different stages after vaccination of rabbit with HPV11N4C-L1 VLPs. Vaccination times are indicated with arrows. The titer of neutralizing antibodies reached a peak level of $10^5$, 1-2 months after a booster.

Neutralization titers of the anti-serums were evaluated using a pseudovirion-based neutralization cell model assay. As shown in FIG. 5, the vaccine produced by mixing HPV11N4C-L1 VLPs prepared in Example 4, could induce neutralizing antibodies with a high titer in animals, and could be used as an effective vaccine for the prevention of HPV infection.

Measurement of Immune Protection of Rhesus Monkeys Vaccinated with HPV6/11 Bivalent Vaccine Four SPF BALB/c mice, 4-5 weeks old, were used. HPV6N5C-L1 VLPs and HPV11N4C-L1 VLPs, which were prepared according to the method similar to that of Examples 1-4, were mixed at a ratio of 1:2 (by weight), wherein the final concentrations of them were 40 μg/mL and 80 μg/mL, respectively. The vaccine was mixed with an equal amount of complete Freund's adjuvant for the first immunization, and was mixed with an equal amount of incomplete Freund's adjuvant for the booster.

Mice were immunized by muscle injection. The amount for the first immunization was 10 μg HPV6N5C-L1 and 20 μg HPV11N4C-L1 per mouse. The booster was administered every two weeks. The amount for the booster was 2 μg HPV6N5C-L1 and 40 μg HPV11N4C-L1 per mouse.

After immunization, external vein blood was collected every week and serum was separated. The titers of neutralizing antibodies against HPV6 and HPV11 in immunized mice were separately determined according to the method of Example 5.

Figure 6:
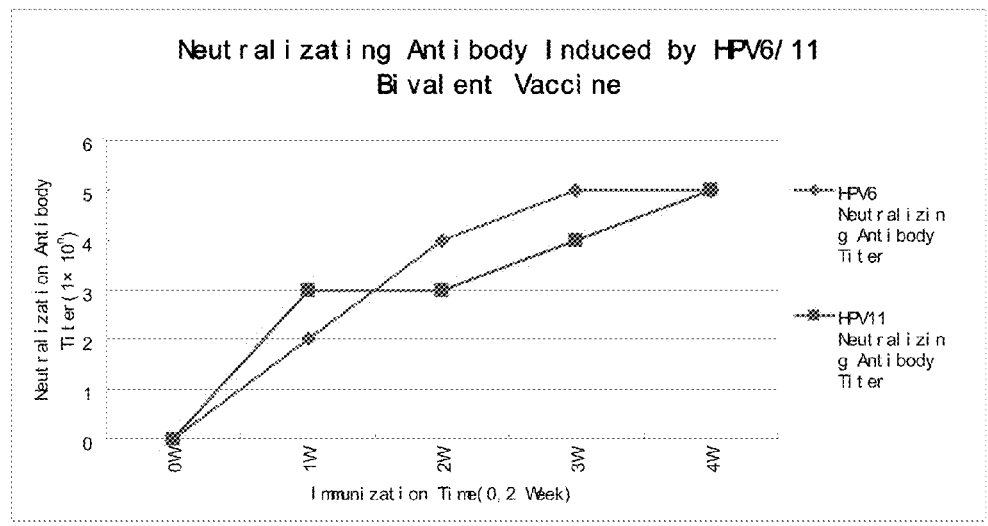
FIG. 6 shows the titers of neutralizing antibodies against HPV 6 and HPV11 in serum at different times after vaccination of mice with HPV6/11 bivalent vaccine obtained in Example 5. Vaccine was administered at 0 and 2 weeks. The titers of neutralizing antibodies against HPV6 and HPV 11 increased rapidly after the first vaccination, reaching $10^4$-$10^5$.

Results were shown in FIG. 6, indicating that HPV6/11 bivalent vaccine, prepared by blending HPV6N5C-L1 and HPV11N4C-L1 VLPs prepared according to the method as described in Examples 1-4, had good immunogenicity, could induce neutralizing antibodies with a high titer against HPV 6 and HPV 11 in animals, and could be used as an effective vaccine for the prevention of HPV6/HPV11 infection (besides the Freund's adjuvants used in the experiments, the vaccine may be prepared by blending the two VLPs of HPV16N5C-L1 and HPV11N4C-L1 with aluminum hydroxide or aluminum phosphate adjuvants available commercially or self-prepared).

The Amino Acid Sequence of L1 of HPV6N5C-L1 is showed in SEQ ID NO: 7 as follows.

```
Met Asp Ser Thr Val Tyr Val Pro Pro Pro Asn Pro Val Ser Lys Val
1               5                   10                  15

Val Ala Thr Asp Ala Tyr Val Thr Arg Thr Asn Ile Phe Tyr His Ala
            20                  25                  30

Ser Ser Ser Arg Leu Leu Ala Val Gly His Pro Tyr Phe Ser Ile Lys
        35                  40                  45

Arg Ala Asn Lys Thr Val Val Pro Lys Val Ser Gly Tyr Gln Tyr Arg
    50                  55                  60

Val Phe Lys Val Val Leu Pro Asp Pro Asn Lys Phe Ala Leu Pro Asp
65                  70                  75                  80

Ser Ser Leu Phe Asp Pro Thr Thr Gln Arg Leu Val Trp Ala Cys Thr
                85                  90                  95

Gly Leu Glu Val Gly Arg Gly Gln Pro Leu Gly Val Gly Val Ser Gly
                100                 105                 110

His Pro Phe Leu Asn Lys Tyr Asp Asp Val Glu Asn Ser Gly Ser Gly
            115                 120                 125

Gly Asn Pro Gly Gln Asp Asn Arg Val Asn Val Gly Met Asp Tyr Lys
    130                 135                 140

Gln Thr Gln Leu Cys Met Val Gly Cys Ala Pro Pro Leu Gly Glu His
145                 150                 155                 160

Trp Gly Lys Gly Lys Gln Cys Thr Asn Thr Pro Val Gln Ala Gly Asp
                165                 170                 175

Cys Pro Pro Leu Glu Leu Ile Thr Ser Val Ile Gln Asp Gly Asp Met
            180                 185                 190

Val Asp Thr Gly Phe Gly Ala Met Asn Phe Ala Asp Leu Gln Thr Asn
            195                 200                 205

Lys Ser Asp Val Pro Ile Asp Ile Cys Gly Thr Thr Cys Lys Tyr Pro
    210                 215                 220

Asp Tyr Leu Gln Met Ala Ala Asp Pro Tyr Gly Asp Arg Leu Phe Phe
225                 230                 235                 240
```

-continued

```
Phe Leu Arg Lys Glu Gln Met Phe Ala Arg His Phe Phe Asn Arg Ala
                245                 250                 255

Gly Glu Val Gly Glu Pro Val Pro Asp Thr Leu Ile Ile Lys Gly Ser
            260                 265                 270

Gly Asn Arg Thr Ser Val Gly Ser Ser Ile Tyr Val Asn Thr Pro Ser
        275                 280                 285

Gly Ser Leu Val Ser Ser Glu Ala Gln Leu Phe Asn Lys Pro Tyr Trp
    290                 295                 300

Leu Gln Lys Ala Gln Gly His Asn Asn Gly Ile Cys Trp Gly Asn Gln
305                 310                 315                 320

Leu Phe Val Thr Val Val Asp Thr Thr Arg Ser Thr Asn Met Thr Leu
                325                 330                 335

Cys Ala Ser Val Thr Thr Ser Ser Thr Tyr Thr Asn Ser Asp Tyr Lys
                340                 345                 350

Glu Tyr Met Arg His Val Glu Glu Tyr Asp Leu Gln Phe Ile Phe Gln
            355                 360                 365

Leu Cys Ser Ile Thr Leu Ser Ala Glu Val Val Ala Tyr Ile His Thr
        370                 375                 380

Met Asn Pro Ser Val Leu Glu Asp Trp Asn Phe Gly Leu Ser Pro Pro
385                 390                 395                 400

Pro Asn Gly Thr Leu Glu Asp Thr Tyr Arg Tyr Val Gln Ser Gln Ala
                405                 410                 415

Ile Thr Cys Gln Lys Pro Thr Pro Glu Lys Gln Lys Pro Asp Pro Tyr
            420                 425                 430

Lys Asn Leu Ser Phe Trp Glu Val Asn Leu Lys Glu Lys Phe Ser Ser
        435                 440                 445

Glu Leu Asp Gln Tyr Pro Leu Gly Arg Lys Phe Leu Leu Gln Ser Gly
    450                 455                 460

Tyr Arg Gly Arg Ser Ser Ile Arg Thr Gly Val Lys Arg Pro Ala Val
465                 470                 475                 480

Ser Lys Ala Ser Ala Ala Pro Lys Arg Lys Arg Ala Lys Thr Lys Arg
                485                 490                 495
```

Measurement of Immune protection of mice vaccinated with HPV6/11/16/18 Quadrivalent Vaccine Four SPF BALB/c mice, 4-5 weeks old, were used. HPV6N5C-L1, HPV11N4C-L1, HPV16N30C-L1 and HPV18N65C-L1 VLPs, prepared according to the method similar to that of Examples 1-4, were mixed at a ratio of 1:2:2:1 (by weight), wherein the final concentrations of them were 40 μg/mL, 80 μg/mL, 80 μg/mL and 40 μg/mL, respectively. The vaccine was mixed with an equal amount of complete Freund's adjuvant for the first immunization, and was mixed with an equal amount of incomplete Freund's adjuvant for the booster.

Mice were immunized by muscle injection. The amount for the first immunization was 10 μg HPV6N5C-L1, 10 μg HPV18N65C-L1, 20 μg HPV11N4C-L1, and 20 μg HPV16N30C-L1 per mouse. The booster was administered every two weeks. The amount for the booster was 20 μg HPV6N5C-L1, 20 μg HPV18N65C-L1, 40 μg HPV11N4C-L1, and 40 μg HPV16N30C-L1 per mouse.

After immunization, external vein blood was collected every week and serum was separated. The titers of neutralizing antibodies against HPV6, HPV11, HPV16 and HPV 18 in immunized mice were separately determined according to the method of Example 5.

Figure 7:
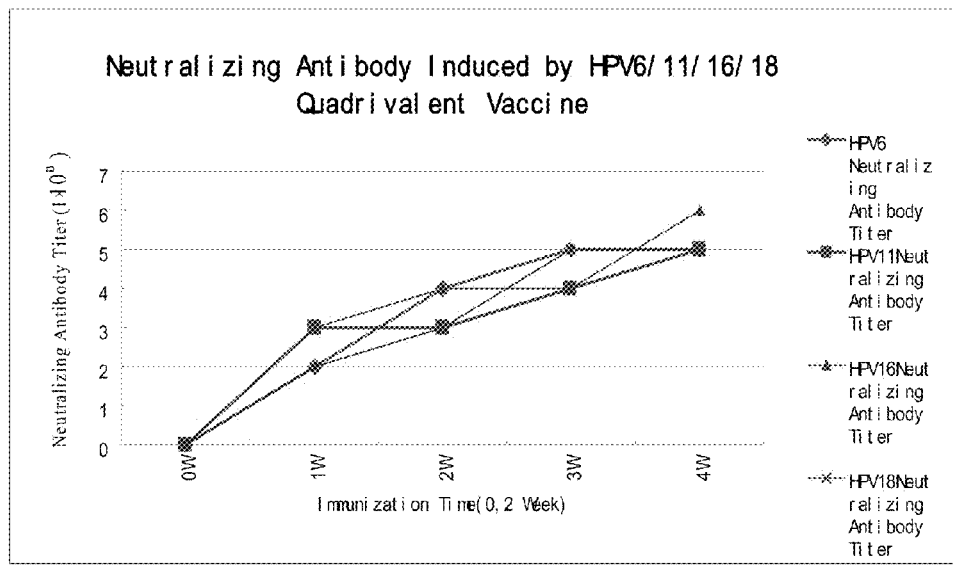
FIG. 7 shows the titers of neutralizing antibodies against HPV 6, HPV 11, HPV 16 and HPV 18 in serum at different times after vaccination of mice with HPV6/11/16/18 quadrivalent vaccine obtained in Example 5. Vaccine was administered at 0 and 2 weeks. The titers of neutralizing antibodies against HPV 6, HPV 11, HPV 16 and HPV 18 increased rapidly after the first vaccination, reaching $10^5$-$10^6$.

Results were shown in FIG. 7, indicating that HPV6/11/16/18 quadrivalent vaccine, prepared by blending HPV6N5C-L1, HPV11N4C-L1, HPV16N30C-L1 and HPV18N65C-L1 VLPs prepared according to the method as described in Examples 1-4, had good immunogenicity, could induce neutralizing antibodies with a high titer against HPV 6, HPV 11, HPV 16, and HPV 18 in animals, and could be used as a effective vaccine for the prevention of HPV6/HPV11/HPV16/HPV18 infection (besides the Freund's adjuvants used in the experiments, the vaccine may be prepared by blending the four VLPs of HPV6N5C-L1, HPV11N4C-L1, HPV16N30C-L1 and HPV18N65C-L1 VLPs with aluminum hydroxide or aluminum phosphate adjuvants available commercially or self-prepared).

The Amino Acid Sequence of L1 of HPV16N30C-L1 is showed in SEQ ID NO 8 as follows.

```
Met Leu Pro Ser Glu Ala Thr Val Tyr Leu Pro Pro Val Pro Val Ser
1               5                   10                  15

Lys Val Val Ser Thr Asp Glu Tyr Val Ala Arg Thr Asn Ile Tyr Tyr
            20                  25                  30
```

-continued

```
His Ala Gly Thr Ser Arg Leu Leu Ala Val Gly His Pro Tyr Phe Pro
         35                  40                  45

Ile Lys Lys Pro Asn Asn Lys Ile Leu Val Pro Lys Val Ser Gly
 50                  55                  60

Leu Gln Tyr Arg Val Phe Arg Ile His Leu Pro Asp Pro Asn Lys Phe
 65                  70                  75                  80

Gly Phe Pro Asp Thr Ser Phe Tyr Asn Pro Asp Thr Gln Arg Leu Val
                 85                  90                  95

Trp Ala Cys Val Gly Val Glu Val Gly Arg Gly Gln Pro Leu Gly Val
            100                 105                 110

Gly Ile Ser Gly His Pro Leu Leu Asn Lys Leu Asp Asp Thr Glu Asn
            115                 120                 125

Ala Ser Ala Tyr Ala Ala Asn Ala Gly Val Asp Asn Arg Glu Cys Ile
        130                 135                 140

Ser Met Asp Tyr Lys Gln Thr Gln Leu Cys Leu Ile Gly Cys Lys Pro
145                 150                 155                 160

Pro Ile Gly Glu His Trp Gly Lys Gly Ser Pro Cys Thr Asn Val Ala
                165                 170                 175

Val Asn Pro Gly Asp Cys Pro Pro Leu Glu Leu Ile Asn Thr Val Ile
            180                 185                 190

Gln Asp Gly Asp Met Val Asp Thr Gly Phe Gly Ala Met Asp Phe Thr
        195                 200                 205

Thr Leu Gln Ala Asn Lys Ser Glu Val Pro Leu Asp Ile Cys Thr Ser
210                 215                 220

Ile Cys Lys Tyr Pro Asp Tyr Ile Lys Met Val Ser Glu Pro Tyr Gly
225                 230                 235                 240

Asp Ser Leu Phe Phe Tyr Leu Arg Arg Glu Gln Met Phe Val Arg His
                245                 250                 255

Leu Phe Asn Arg Ala Gly Ala Val Gly Asp Asn Val Pro Asp Asp Leu
            260                 265                 270

Tyr Ile Lys Gly Ser Gly Ser Thr Ala Asn Leu Ala Ser Ser Asn Tyr
        275                 280                 285

Phe Pro Thr Pro Ser Gly Ser Met Val Thr Ser Asp Ala Gln Ile Phe
290                 295                 300

Asn Lys Pro Tyr Trp Leu Gln Arg Ala Gln Gly His Asn Asn Gly Ile
305                 310                 315                 320

Cys Trp Gly Asn Gln Leu Phe Val Thr Val Val Asp Thr Thr Arg Ser
                325                 330                 335

Thr Asn Met Ser Leu Cys Ala Ala Ile Ser Thr Ser Glu Thr Thr Tyr
            340                 345                 350

Lys Asn Thr Asn Phe Lys Glu Tyr Leu Arg His Gly Glu Glu Tyr Asp
        355                 360                 365

Leu Gln Phe Ile Phe Gln Leu Cys Lys Ile Thr Leu Thr Ala Asp Ile
370                 375                 380

Met Thr Tyr Ile His Ser Met Asn Ser Thr Ile Leu Glu Asp Trp Asn
385                 390                 395                 400

Phe Gly Leu Gln Pro Pro Gly Gly Thr Leu Glu Asp Thr Tyr Arg
                405                 410                 415

Phe Val Thr Ser Gln Ala Ile Ala Cys Gln Lys His Thr Pro Pro Ala
            420                 425                 430

Pro Lys Glu Asp Pro Leu Lys Lys Tyr Thr Phe Trp Glu Val Asn Leu
        435                 440                 445

Lys Glu Lys Phe Ser Ala Asp Leu Asp Gln Phe Pro Leu Gly Arg Lys
450                 455                 460
```

-continued

```
Phe Leu Leu Gln Ala Gly Leu Glu Ala Lys Pro Lys Phe Thr Leu Gly
465                 470                 475                 480

Lys Arg Lys Ala Thr Pro Thr Thr Ser Ser Thr Ser Thr Thr Ala Lys
                485                 490                 495

Arg Lys Lys Arg Lys Leu
            500
```

The Amino Acid Sequence of L1 of HPV18N65C-L1 is showed in SEQ ID NO 9 as follows.

```
Met Arg Pro Ser Asp Asn Thr Val Tyr Leu Pro Pro Ser Val Ala
1               5                   10                  15

Arg Val Val Asn Thr Asp Asp Tyr Val Thr Arg Thr Ser Ile Phe Tyr
                20                  25                  30

His Ala Gly Ser Ser Arg Leu Leu Thr Val Gly Asn Pro Tyr Phe Arg
            35                  40                  45

Val Pro Ala Gly Gly Gly Asn Lys Gln Asp Ile Pro Lys Val Ser Ala
        50                  55                  60

Tyr Gln Tyr Arg Val Phe Arg Val Gln Leu Pro Asp Pro Asn Lys Phe
65                  70                  75                  80

Gly Leu Pro Asp Thr Ser Ile Tyr Asn Pro Glu Thr Gln Arg Leu Val
                85                  90                  95

Trp Ala Cys Ala Gly Val Glu Ile Gly Arg Gly Gln Pro Leu Gly Val
                100                 105                 110

Gly Leu Ser Gly His Pro Phe Tyr Asn Lys Leu Asp Asp Thr Glu Ser
            115                 120                 125

Ser His Ala Ala Thr Ser Asn Val Ser Glu Asp Val Arg Asp Asn Val
    130                 135                 140

Ser Val Asp Tyr Lys Gln Thr Gln Leu Cys Ile Leu Gly Cys Ala Pro
145                 150                 155                 160

Ala Ile Gly Glu His Trp Ala Lys Gly Thr Ala Cys Lys Ser Arg Pro
                165                 170                 175

Leu Ser Gln Gly Asp Cys Pro Pro Leu Glu Leu Lys Asn Thr Val Leu
            180                 185                 190

Glu Asp Gly Asp Met Val Asp Thr Gly Tyr Gly Ala Met Asp Phe Ser
        195                 200                 205

Thr Leu Gln Asp Thr Lys Cys Glu Val Pro Leu Asp Ile Cys Gln Ser
    210                 215                 220

Ile Cys Lys Tyr Pro Asp Tyr Leu Gln Met Ser Ala Asp Pro Tyr Gly
225                 230                 235                 240

Asp Ser Met Phe Phe Cys Leu Arg Arg Glu Gln Leu Phe Ala Arg His
                245                 250                 255

Phe Trp Asn Arg Ala Gly Thr Met Gly Asp Thr Val Pro Gln Ser Leu
            260                 265                 270

Tyr Ile Lys Gly Thr Gly Met Arg Ala Ser Pro Gly Ser Cys Val Tyr
        275                 280                 285

Ser Pro Ser Pro Ser Gly Ser Ile Val Thr Ser Asp Ser Gln Leu Phe
    290                 295                 300

Asn Lys Pro Tyr Trp Leu His Lys Ala Gln Gly His Asn Asn Gly Val
305                 310                 315                 320

Cys Trp His Asn Gln Leu Phe Val Thr Val Asp Thr Thr Arg Ser
                325                 330                 335

Thr Asn Leu Thr Ile Cys Ala Ser Thr Gln Ser Pro Val Pro Gly Gln
            340                 345                 350
```

```
Tyr Asp Ala Thr Lys Phe Lys Gln Tyr Ser Arg His Val Glu Glu Tyr
            355                 360                 365

Asp Leu Gln Phe Ile Phe Gln Leu Cys Thr Ile Thr Leu Thr Ala Asp
        370                 375                 380

Val Met Ser Tyr Ile His Ser Met Asn Ser Ser Ile Leu Glu Asp Trp
385                 390                 395                 400

Asn Phe Gly Val Pro Pro Pro Thr Thr Ser Leu Val Asp Thr Tyr
                405                 410                 415

Arg Phe Val Gln Ser Val Ala Ile Ala Cys Gln Lys Asp Ala Ala Pro
            420                 425                 430

Ala Glu Asn Lys Asp Pro Tyr Asp Lys Leu Lys Phe Trp Asn Val Asp
        435                 440                 445

Leu Lys Glu Lys Phe Ser Leu Asp Leu Asp Gln Tyr Pro Leu Gly Arg
    450                 455                 460

Lys Phe Leu Val Gln Ala Gly Leu Arg Arg Lys Pro Thr Ile Gly Pro
465                 470                 475                 480

Arg Lys Arg Ser Ala Pro Ser Ala Thr Thr Ala Ser Lys Pro Ala Lys
            485                 490                 495

Arg Val Arg Val Arg Ala Arg Lys
            500
```

The Amino Acid Sequence of L1 of HPV6N5C-L1 VLP is shown in SEQ ID NO:7, as described above.

EXAMPLE 6

Figure 8:
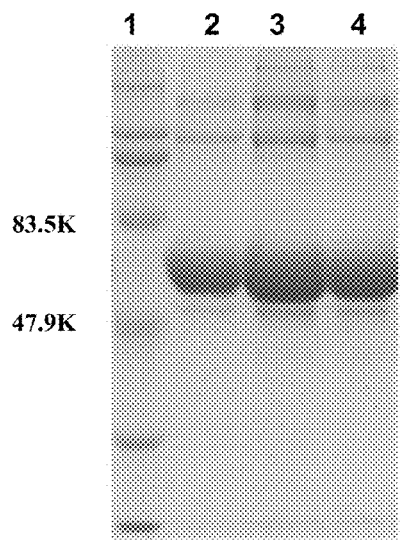
FIG. 8 shows the SDS-PAGE results of HPV11N3C-L1, HPV11N5C-L1 and HPV11N6C-L1 protein separately having 3, 5 and 6 amino acids truncated at the N-terminal of HPV 11 L1 protein (the amino acid sequences thereof set forth in SEQ ID Nos: 2, 3 and 4, respectively) during steps a)-e) of the method according to the invention. Lane 1: Molecular Weight Marker; Lane 2: HPV11N3C-L1 purified according to step a)-e), 10 μL; Lane 3: HPV11N5C-L1 purified according to step a)-e), 10 μL; Lane 4: HPV11N6C-L1 purified according to step a)-e), 10 μL. The result shows that the purity of HPV11N3C-L1, HPV11N5C-L1 and HPV11N6C-L1 protein having 3, 5 and 6 amino acids truncated at the N-terminal of HPV 11 L1 protein respectively, reached about 95% following the steps a)-e).
Figure 9:
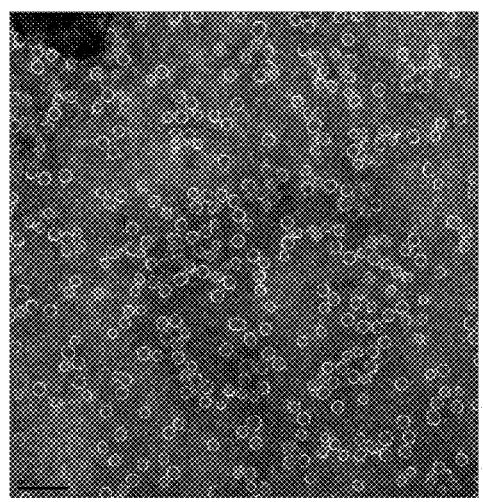
FIG. 9 the transmission electron microscopy (TEM) photographs of the VLPs of HPV11N3C-L1, HPV11N5C-L1 and HPV11N6C-L1 protein separately having 3, 5 and 6 amino acids truncated at the N-terminal of HPV 11 L1 protein obtained following steps a)-f), taken at 50,000× magnification. 1. The transmission electron microscopy (TEM) photographs of HPV11N3C-L1 VLPs obtained following steps a)-f). 2. The transmission electron microscopy (TEM) photographs of HPV11N5C-L1 VLPs obtained following steps a)-f). 3. The transmission electron microscopy (TEM) photographs of HPV11N6C-L1 VLPs obtained following steps a)-f). The results show that a great deal of VLPs in a radius of about 25 nm were observed in visual field, wherein the particle size was consistant with the theoretic size and the particles were homogenous.
Figure 9:
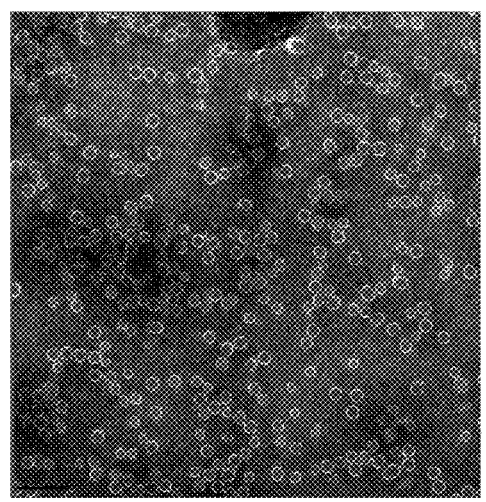
Figure 9:
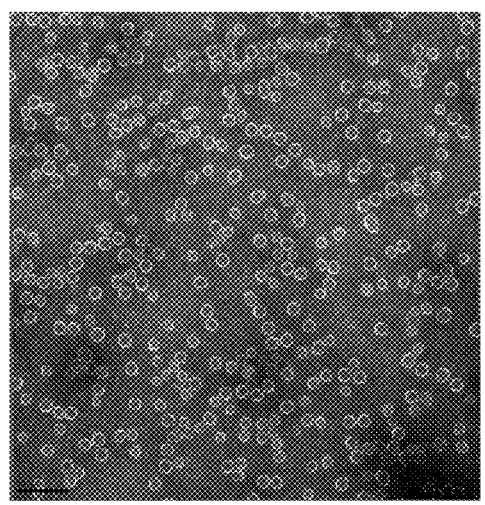
Figure 10:
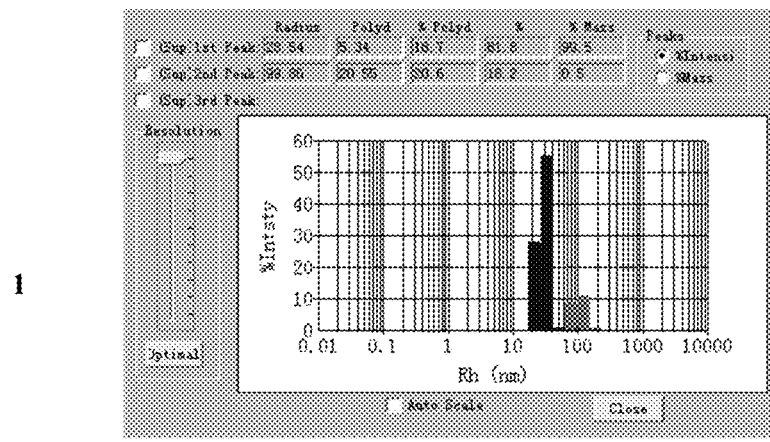
FIG. 10 shows the dynamic light-scattering measurement result of the VLPs of HPV11N3C-L1, HPV11N5C-L1 and HPV11N6C-L1 protein separately having 3, 5 and 6 amino acids truncated at the N-terminal of HPV 11 L1 protein obtained following steps a)-f). 1. The dynamic light-scattering measurement result of HPV11N3C-L1 VLPs obtained following steps a)-f). 2. The dynamic light-scattering measurement result of HPV11N5C-L1 VLPs obtained following steps a)-f). 3. The dynamic light-scattering measurement result of HPV11N6C-L1 VLPs obtained following steps a)-f). The result shows that HPV11N3C-L1 VLPs, HPV11N5C-L1 VLPs and HPV11N6C-L1 VLPs had a hydrodynamic radius of about 25 nm and a particle assembly rate of above 80%.
Figure 10:
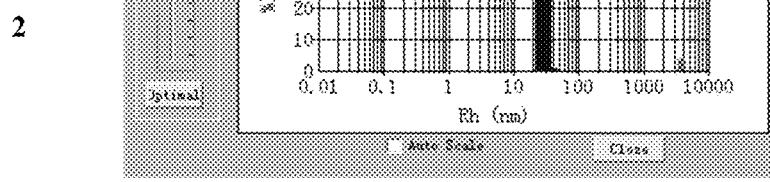
Figure 10:
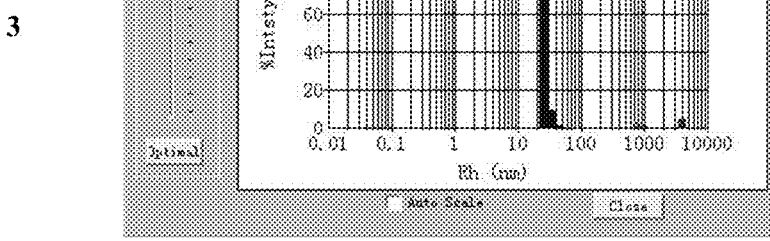

The truncated HPV11L1 proteins set forth in SEQ ID NOs: 2, 3 and 4 were prepared according to the techniques used in examples 1-5. All these truncated proteins could be purified to an extent of above 98% and could be assembled into VLPs with a radius of about 25 nm. The results are shown in FIGS. 8, 9 and 10.

---

The invention claimed is:

1. A vaccine for prevention of condyloma acuminatum or HPV infections, comprising vaccine A or vaccine B:
   wherein the vaccine A comprises:
   (A1) HPV11 VLP comprising a protein consisting of the amino acid sequence set forth in SEQ ID NO: 1;
   (A2) HPV6 VLP comprising a protein consisting of the amino acid sequence set forth in SEQ ID NO: 7; and
   (A3) carriers or excipients useful for vaccines; and
   wherein the vaccine B comprises:
   (B1) HPV11 VLP comprising a protein consisting of the amino acid sequence set forth in SEQ ID NO: 1;
   (B2) HPV6 VLP comprising a protein consisting of the amino acid sequence set forth in SEQ ID NO: 7;
   (B3) HPV16 VLP comprising a protein consisting of the amino acid sequence set forth in SEQ ID NO: 8;
   (B4) HPV18 VLP comprising a protein consisting of the amino acid sequence set forth in SEQ ID NO: 9; and
   (B5) carriers or excipients useful for vaccines.

2. The vaccine as claimed in claim 1, wherein the vaccine comprises the HPV6 VLP and the HPV11 VLP.

3. The vaccine as claimed in claim 2, wherein the vaccine comprises a combination of the HPV6 VLP, the HPV11 VLP, the HPV 16 VLP and the HPV 18 VLP.

4. A method for preventing condyloma acuminatum or HPV infections, comprising administering a vaccine comprising a preventively effective amount of the vaccine according to claim 1, to an individual in need of preventing condyloma acuminatum or HPV infections.

* * * * *

SEQUENCE LISTING

```
<160> NUMBER OF SEQ ID NOS: 11

<210> SEQ ID NO 1
<211> LENGTH: 498
<212> TYPE: PRT
<213> ORGANISM: Artificial
<220> FEATURE:
<223> OTHER INFORMATION: Truncated HPV11 L1 protein

<400> SEQUENCE: 1

Met Ser Asp Ser Thr Val Tyr Val Pro Pro Asn Pro Val Ser Lys
1               5                   10                  15

Val Val Ala Thr Asp Ala Tyr Val Lys Arg Thr Asn Ile Phe Tyr His
            20                  25                  30

Ala Ser Ser Ser Arg Leu Leu Ala Val Gly His Pro Tyr Tyr Ser Ile
        35                  40                  45

Lys Lys Val Asn Lys Thr Val Val Pro Lys Val Ser Gly Tyr Gln Tyr
    50                  55                  60

Arg Val Phe Lys Val Val Leu Pro Asp Pro Asn Lys Phe Ala Leu Pro
65                  70                  75                  80

Asp Ser Ser Leu Phe Asp Pro Thr Thr Gln Arg Leu Val Trp Ala Cys
                85                  90                  95

Thr Gly Leu Glu Val Gly Arg Gly Gln Pro Leu Gly Val Gly Val Ser
            100                 105                 110

Gly His Pro Leu Leu Asn Lys Tyr Asp Asp Val Glu Asn Ser Gly Gly
        115                 120                 125

Tyr Gly Gly Asn Pro Gly Gln Asp Asn Arg Val Asn Val Gly Met Asp
```

130                 135                 140
Tyr Lys Gln Thr Gln Leu Cys Met Val Gly Cys Ala Pro Pro Leu Gly
145                 150                 155                 160

Glu His Trp Gly Lys Gly Thr Gln Cys Ser Asn Thr Ser Val Gln Asn
                165                 170                 175

Gly Asp Cys Pro Pro Leu Glu Leu Ile Thr Ser Val Ile Gln Asp Gly
            180                 185                 190

Asp Met Val Asp Thr Gly Phe Gly Ala Met Asn Phe Ala Asp Leu Gln
        195                 200                 205

Thr Asn Lys Ser Asp Val Pro Leu Asp Ile Cys Gly Thr Val Cys Lys
    210                 215                 220

Tyr Pro Asp Tyr Leu Gln Met Ala Ala Asp Pro Tyr Gly Asp Arg Leu
225                 230                 235                 240

Phe Phe Tyr Leu Arg Lys Glu Gln Met Phe Ala Arg His Phe Phe Asn
                245                 250                 255

Arg Ala Gly Thr Val Gly Glu Pro Val Pro Asp Asp Leu Leu Val Lys
            260                 265                 270

Gly Gly Asn Asn Arg Ser Ser Val Ala Ser Ser Ile Tyr Val His Thr
        275                 280                 285

Pro Ser Gly Ser Leu Val Ser Ser Glu Ala Gln Leu Phe Asn Lys Pro
    290                 295                 300

Tyr Trp Leu Gln Lys Ala Gln Gly His Asn Asn Gly Ile Cys Trp Gly
305                 310                 315                 320

Asn His Leu Phe Val Thr Val Val Asp Thr Thr Arg Ser Thr Asn Met
                325                 330                 335

Thr Leu Cys Ala Ser Val Ser Lys Ser Ala Thr Tyr Thr Asn Ser Asp
            340                 345                 350

Tyr Lys Glu Tyr Met Arg His Val Glu Glu Phe Asp Leu Gln Phe Ile
        355                 360                 365

Phe Gln Leu Cys Ser Ile Thr Leu Ser Ala Glu Val Met Ala Tyr Ile
    370                 375                 380

His Thr Met Asn Pro Ser Val Leu Glu Asp Trp Asn Phe Gly Leu Ser
385                 390                 395                 400

Pro Pro Pro Asn Gly Thr Leu Glu Asp Thr Tyr Arg Tyr Val Gln Ser
                405                 410                 415

Gln Ala Ile Thr Cys Gln Lys Pro Thr Pro Glu Lys Glu Lys Gln Asp
            420                 425                 430

Pro Tyr Lys Asp Met Ser Phe Trp Glu Val Asn Leu Lys Glu Lys Phe
        435                 440                 445

Ser Ser Glu Leu Asp Gln Phe Pro Leu Gly Arg Lys Phe Leu Leu Gln
    450                 455                 460

Ser Gly Tyr Arg Gly Arg Thr Ser Ala Arg Thr Gly Ile Lys Arg Pro
465                 470                 475                 480

Ala Val Ser Lys Pro Ser Thr Ala Pro Lys Arg Lys Arg Thr Lys Thr
                485                 490                 495

Lys Lys

<210> SEQ ID NO 2
<211> LENGTH: 499
<212> TYPE: PRT
<213> ORGANISM: Artificial
<220> FEATURE:
<223> OTHER INFORMATION: Truncated HPV11 L1 protein

<400> SEQUENCE: 2

```
Met Pro Ser Asp Ser Thr Val Tyr Val Pro Pro Asn Pro Val Ser
1               5                   10                  15

Lys Val Val Ala Thr Asp Ala Tyr Val Lys Arg Thr Asn Ile Phe Tyr
            20                  25                  30

His Ala Ser Ser Arg Leu Leu Ala Val Gly His Pro Tyr Tyr Ser
        35                  40                  45

Ile Lys Lys Val Asn Lys Thr Val Val Pro Lys Val Ser Gly Tyr Gln
    50                  55                  60

Tyr Arg Val Phe Lys Val Val Leu Pro Asp Pro Asn Lys Phe Ala Leu
65                  70                  75                  80

Pro Asp Ser Ser Leu Phe Asp Pro Thr Thr Gln Arg Leu Val Trp Ala
                85                  90                  95

Cys Thr Gly Leu Glu Val Gly Arg Gly Gln Pro Leu Gly Val Gly Val
                100                 105                 110

Ser Gly His Pro Leu Leu Asn Lys Tyr Asp Asp Val Glu Asn Ser Gly
            115                 120                 125

Gly Tyr Gly Gly Asn Pro Gly Gln Asp Asn Arg Val Asn Val Gly Met
        130                 135                 140

Asp Tyr Lys Gln Thr Gln Leu Cys Met Val Gly Cys Ala Pro Pro Leu
145                 150                 155                 160

Gly Glu His Trp Gly Lys Gly Thr Gln Cys Ser Asn Thr Ser Val Gln
                165                 170                 175

Asn Gly Asp Cys Pro Pro Leu Glu Leu Ile Thr Ser Val Ile Gln Asp
            180                 185                 190

Gly Asp Met Val Asp Thr Gly Phe Gly Ala Met Asn Phe Ala Asp Leu
        195                 200                 205

Gln Thr Asn Lys Ser Asp Val Pro Leu Asp Ile Cys Gly Thr Val Cys
210                 215                 220

Lys Tyr Pro Asp Tyr Leu Gln Met Ala Ala Asp Pro Tyr Gly Asp Arg
225                 230                 235                 240

Leu Phe Phe Tyr Leu Arg Lys Glu Gln Met Phe Ala Arg His Phe Phe
                245                 250                 255

Asn Arg Ala Gly Thr Val Gly Glu Pro Val Pro Asp Asp Leu Leu Val
            260                 265                 270

Lys Gly Gly Asn Asn Arg Ser Ser Val Ala Ser Ser Ile Tyr Val His
        275                 280                 285

Thr Pro Ser Gly Ser Leu Val Ser Ser Glu Ala Gln Leu Phe Asn Lys
        290                 295                 300

Pro Tyr Trp Leu Gln Lys Ala Gln Gly His Asn Asn Gly Ile Cys Trp
305                 310                 315                 320

Gly Asn His Leu Phe Val Thr Val Val Asp Thr Thr Arg Ser Thr Asn
                325                 330                 335

Met Thr Leu Cys Ala Ser Val Ser Lys Ser Ala Thr Thr Tyr Asn Ser
            340                 345                 350

Asp Tyr Lys Glu Tyr Met Arg His Val Glu Glu Phe Asp Leu Gln Phe
        355                 360                 365

Ile Phe Gln Leu Cys Ser Ile Thr Leu Ser Ala Glu Val Met Ala Tyr
    370                 375                 380

Ile His Thr Met Asn Pro Ser Val Leu Glu Asp Trp Asn Phe Gly Leu
385                 390                 395                 400

Ser Pro Pro Pro Asn Gly Thr Leu Glu Asp Thr Tyr Arg Tyr Val Gln
                405                 410                 415
```

```
Ser Gln Ala Ile Thr Cys Gln Lys Pro Thr Pro Glu Lys Glu Lys Gln
                420                 425                 430

Asp Pro Tyr Lys Asp Met Ser Phe Trp Glu Val Asn Leu Lys Glu Lys
                435                 440                 445

Phe Ser Ser Glu Leu Asp Gln Phe Pro Leu Gly Arg Lys Phe Leu Leu
                450                 455                 460

Gln Ser Gly Tyr Arg Gly Arg Thr Ser Ala Arg Thr Gly Ile Lys Arg
465                 470                 475                 480

Pro Ala Val Ser Lys Pro Ser Thr Ala Pro Lys Arg Lys Arg Thr Lys
                485                 490                 495

Thr Lys Lys

<210> SEQ ID NO 3
<211> LENGTH: 497
<212> TYPE: PRT
<213> ORGANISM: Artificial
<220> FEATURE:
<223> OTHER INFORMATION: Truncated HPV11 L1 protein

<400> SEQUENCE: 3

Met Asp Ser Thr Val Tyr Val Pro Pro Asn Pro Val Ser Lys Val Val
1               5                   10                  15

Val Ala Thr Asp Ala Tyr Val Lys Arg Thr Asn Ile Phe Tyr His Ala
                20                  25                  30

Ser Ser Ser Arg Leu Leu Ala Val Gly His Pro Tyr Tyr Ser Ile Lys
                35                  40                  45

Lys Val Asn Lys Thr Val Val Pro Lys Val Ser Gly Tyr Gln Tyr Arg
            50                  55                  60

Val Phe Lys Val Val Leu Pro Asp Pro Asn Lys Phe Ala Leu Pro Asp
65                  70                  75                  80

Ser Ser Leu Phe Asp Pro Thr Thr Gln Arg Leu Val Trp Ala Cys Thr
                85                  90                  95

Gly Leu Glu Val Gly Arg Gly Gln Pro Leu Gly Val Gly Val Ser Gly
                100                 105                 110

His Pro Leu Leu Asn Lys Tyr Asp Asp Val Glu Asn Ser Gly Gly Tyr
                115                 120                 125

Gly Gly Asn Pro Gly Gln Asp Asn Arg Val Asn Val Gly Met Asp Tyr
            130                 135                 140

Lys Gln Thr Gln Leu Cys Met Val Gly Cys Ala Pro Pro Leu Gly Glu
145                 150                 155                 160

His Trp Gly Lys Gly Thr Gln Cys Ser Asn Thr Ser Val Gln Asn Gly
                165                 170                 175

Asp Cys Pro Pro Leu Glu Leu Ile Thr Ser Val Ile Gln Asp Gly Asp
                180                 185                 190

Met Val Asp Thr Gly Phe Gly Ala Met Asn Phe Ala Asp Leu Gln Thr
            195                 200                 205

Asn Lys Ser Asp Val Pro Leu Asp Ile Cys Gly Thr Val Cys Lys Tyr
210                 215                 220

Pro Asp Tyr Leu Gln Met Ala Ala Asp Pro Tyr Gly Asp Arg Leu Phe
225                 230                 235                 240

Phe Tyr Leu Arg Lys Glu Gln Met Phe Ala Arg His Phe Phe Asn Arg
                245                 250                 255

Ala Gly Thr Val Gly Glu Pro Val Pro Asp Asp Leu Leu Val Lys Gly
                260                 265                 270

Gly Asn Asn Arg Ser Ser Val Ala Ser Ser Ile Tyr Val His Thr Pro
```

```
                275                 280                 285
Ser Gly Ser Leu Val Ser Ser Glu Ala Gln Leu Phe Asn Lys Pro Tyr
            290                 295                 300
Trp Leu Gln Lys Ala Gln Gly His Asn Asn Gly Ile Cys Trp Gly Asn
305                 310                 315                 320
His Leu Phe Val Thr Val Val Asp Thr Thr Arg Ser Thr Asn Met Thr
                325                 330                 335
Leu Cys Ala Ser Val Ser Lys Ser Ala Thr Tyr Thr Asn Ser Asp Tyr
            340                 345                 350
Lys Glu Tyr Met Arg His Val Glu Glu Phe Asp Leu Gln Phe Ile Phe
                355                 360                 365
Gln Leu Cys Ser Ile Thr Leu Ser Ala Glu Val Met Ala Tyr Ile His
            370                 375                 380
Thr Met Asn Pro Ser Val Leu Glu Asp Trp Asn Phe Gly Leu Ser Pro
385                 390                 395                 400
Pro Pro Asn Gly Thr Leu Glu Asp Thr Tyr Arg Tyr Val Gln Ser Gln
                405                 410                 415
Ala Ile Thr Cys Gln Lys Pro Thr Pro Glu Lys Glu Lys Gln Asp Pro
            420                 425                 430
Tyr Lys Asp Met Ser Phe Trp Glu Val Asn Leu Lys Glu Lys Phe Ser
                435                 440                 445
Ser Glu Leu Asp Gln Phe Pro Leu Gly Arg Lys Phe Leu Leu Gln Ser
            450                 455                 460
Gly Tyr Arg Gly Arg Thr Ser Ala Arg Thr Gly Ile Lys Arg Pro Ala
465                 470                 475                 480
Val Ser Lys Pro Ser Thr Ala Pro Lys Arg Lys Arg Thr Lys Thr Lys
                485                 490                 495
Lys

<210> SEQ ID NO 4
<211> LENGTH: 496
<212> TYPE: PRT
<213> ORGANISM: Artificial
<220> FEATURE:
<223> OTHER INFORMATION: Truncated HPV11 L1 protein

<400> SEQUENCE: 4

Met Ser Thr Val Tyr Val Pro Pro Asn Pro Val Ser Lys Val Val
1               5                   10                  15
Ala Thr Asp Ala Tyr Val Lys Arg Thr Asn Ile Phe Tyr His Ala Ser
            20                  25                  30
Ser Ser Arg Leu Leu Ala Val Gly His Pro Tyr Tyr Ser Ile Lys Lys
        35                  40                  45
Val Asn Lys Thr Val Val Pro Lys Val Ser Gly Tyr Gln Tyr Arg Val
    50                  55                  60
Phe Lys Val Val Leu Pro Asp Pro Asn Lys Phe Ala Leu Pro Asp Ser
65                  70                  75                  80
Ser Leu Phe Asp Pro Thr Thr Gln Arg Leu Val Trp Ala Cys Thr Gly
                85                  90                  95
Leu Glu Val Gly Arg Gly Gln Pro Leu Gly Val Gly Val Ser Gly His
            100                 105                 110
Pro Leu Leu Asn Lys Tyr Asp Asp Val Glu Asn Ser Gly Gly Tyr Gly
        115                 120                 125
Gly Asn Pro Gly Gln Asp Asn Arg Val Asn Val Gly Met Asp Tyr Lys
    130                 135                 140
```

```
Gln Thr Gln Leu Cys Met Val Gly Cys Ala Pro Pro Leu Gly Glu His
145                 150                 155                 160

Trp Gly Lys Gly Thr Gln Cys Ser Asn Thr Ser Val Gln Asn Gly Asp
                165                 170                 175

Cys Pro Pro Leu Glu Leu Ile Thr Ser Val Ile Gln Asp Gly Asp Met
            180                 185                 190

Val Asp Thr Gly Phe Gly Ala Met Asn Phe Ala Asp Leu Gln Thr Asn
        195                 200                 205

Lys Ser Asp Val Pro Leu Asp Ile Cys Gly Thr Val Cys Lys Tyr Pro
210                 215                 220

Asp Tyr Leu Gln Met Ala Ala Asp Pro Tyr Gly Asp Arg Leu Phe Phe
225                 230                 235                 240

Tyr Leu Arg Lys Glu Gln Met Phe Ala Arg His Phe Phe Asn Arg Ala
                245                 250                 255

Gly Thr Val Gly Glu Pro Val Pro Asp Asp Leu Leu Val Lys Gly Gly
            260                 265                 270

Asn Asn Arg Ser Ser Val Ala Ser Ser Ile Tyr Val His Thr Pro Ser
        275                 280                 285

Gly Ser Leu Val Ser Ser Glu Ala Gln Leu Phe Asn Lys Pro Tyr Trp
290                 295                 300

Leu Gln Lys Ala Gln Gly His Asn Asn Gly Ile Cys Trp Gly Asn His
305                 310                 315                 320

Leu Phe Val Thr Val Val Asp Thr Thr Arg Ser Thr Asn Met Thr Leu
                325                 330                 335

Cys Ala Ser Val Ser Lys Ser Ala Thr Tyr Thr Asn Ser Asp Tyr Lys
            340                 345                 350

Glu Tyr Met Arg His Val Glu Glu Phe Asp Leu Gln Phe Ile Phe Gln
        355                 360                 365

Leu Cys Ser Ile Thr Leu Ser Ala Glu Val Met Ala Tyr Ile His Thr
370                 375                 380

Met Asn Pro Ser Val Leu Glu Asp Trp Asn Phe Gly Leu Ser Pro Pro
385                 390                 395                 400

Pro Asn Gly Thr Leu Glu Asp Thr Tyr Arg Tyr Val Gln Ser Gln Ala
                405                 410                 415

Ile Thr Cys Gln Lys Pro Thr Pro Glu Lys Glu Lys Gln Asp Pro Tyr
            420                 425                 430

Lys Asp Met Ser Phe Trp Glu Val Asn Leu Lys Glu Lys Phe Ser Ser
        435                 440                 445

Glu Leu Asp Gln Phe Pro Leu Gly Arg Lys Phe Leu Leu Gln Ser Gly
    450                 455                 460

Tyr Arg Gly Arg Thr Ser Ala Arg Thr Gly Ile Lys Arg Pro Ala Val
465                 470                 475                 480

Ser Lys Pro Ser Thr Ala Pro Lys Arg Lys Arg Thr Lys Thr Lys Lys
                485                 490                 495

<210> SEQ ID NO 5
<211> LENGTH: 1506
<212> TYPE: DNA
<213> ORGANISM: Artificial
<220> FEATURE:
<223> OTHER INFORMATION: synthetic HPV11 L1 gene

<400> SEQUENCE: 5
atgtggcggc ctagcgacag cacagtatat gtgcctcctc ccaaccctgt atccaaggtt      60
```

| | |
|---|---|
| gttgccacgg atgcgtatgt taaacgcacc aacatatttt atcacgccag cagttctaga | 120 |
| ctccttgctg tgggacatcc atattactct atcaaaaaag ttaacaaaac agttgtacca | 180 |
| aaggtgtctg gatatcaata tagagtgttt aaggtagtgt tgccagatcc taacaagttt | 240 |
| gcattacctg attcatctct gtttgacccc actacacagc gtttagtatg ggcgtgcaca | 300 |
| gggttggagg taggcagggg tcaacccttta ggcgttggtg ttagtgggca tccattgcta | 360 |
| aacaaatatg atgatgtaga aaatagtggt gggtatggtg gtaatcctgg tcaggataat | 420 |
| agggttaatg taggtatgga ttataaacaa acccagctat gtatggtggg ctgtgctcca | 480 |
| ccgttaggtg aacattgggg taagggtaca caatgttcaa atacctctgt acaaaatggt | 540 |
| gactgccccc cgttggaact tattaccagt gttatacagg atggggacat ggttgataca | 600 |
| ggctttggtg ctatgaattt tgcagactta caaaccaata atcggatgt tccccttgat | 660 |
| atttgtggaa ctgtctgcaa atatcctgat tatttgcaaa tggcagcaga cccttatggt | 720 |
| gataggttgt tttttttattt gcgaaaggaa caaatgtttg ctagacactt ttttaatagg | 780 |
| gccggtactg tgggggaacc tgtgcctgat gacctgttgg taaaaggggg taataataga | 840 |
| tcatctgtag ctagtagtat ttatgtacat acacctagtg gctcattggt gtcttcagag | 900 |
| gctcaattat ttaataaacc atattggctt caaaaggctc aggacataa caatggtatt | 960 |
| tgctggggaa accacttgtt tgttactgtg gtagatacca cacgcagtac aaatatgaca | 1020 |
| ctatgtgcat ctgtgtctaa atctgctaca tacactaatt cagattataa ggaatacatg | 1080 |
| cgccatgtgg aagagtttga tttacagttt atttttcaat tgtgtagcat tacattatct | 1140 |
| gcagaagtca tggcctatat acacacaatg aatccttctg ttttggagga ctggaacttt | 1200 |
| ggtttatcgc ctccaccaaa tggtacactg gaggatactt atagatatgt acagtcacag | 1260 |
| gccattacct gtcagaaacc cacacccgaa aagaaaaac aggaccccta taaggatatg | 1320 |
| agttttttggg aggttaactt aaaagaaaag ttttcttatg aattagatca gtttcccctt | 1380 |
| ggacgtaagt ttttattgca aagtggatat cgaggacgga cgtctgctcg tacaggtata | 1440 |
| aagcgcccag ctgtgtctaa gcctctacag gcccccaaac gaaacgtac caaaaccaga | 1500 |
| aagtaa | 1506 |

<210> SEQ ID NO 6
<211> LENGTH: 1497
<212> TYPE: DNA
<213> ORGANISM: Artificial
<220> FEATURE:
<223> OTHER INFORMATION: Nucleic acid encoding truncated HPV11 L1 protein

<400> SEQUENCE: 6

| | |
|---|---|
| atgagcgaca gcacagtata tgtgcctcct cccaaccctg tatccaaggt tgttgccacg | 60 |
| gatgcgtatg ttaaacgcac caacatattt tatcacgcca gcagttctag actccttgct | 120 |
| gtgggacatc catattactc tatcaaaaaa gttaacaaaa cagttgtacc aaaggtgtct | 180 |
| ggatatcaat atagagtgtt taaggtagtg ttgccagatc ctaacaagtt tgcattacct | 240 |
| gattcatctc tgtttgaccc cactacacag cgtttagtat gggcgtgcac agggttggag | 300 |
| gtaggcaggg gtcaaccttt aggcgttggt gttagtgggc atccattgct aaacaaatat | 360 |
| gatgatgtag aaaatagtgg tgggtatggt ggtaatcctg gtcaggataa tagggttaat | 420 |
| gtaggtatgg attataaaca aacccagcta tgtatggtgg ctgtgctcc accgttaggt | 480 |
| gaacattggg gtaagggtac acaatgttca aatacctctg tacaaaatgg tgactgcccc | 540 |

-continued

```
ccgttggaac ttattaccag tgttatacag gatggggaca tggttgatac aggctttggt    600
gctatgaatt ttgcagactt acaaccaat aaatcggatg ttccccttga tatttgtgga    660
actgtctgca aatatcctga ttatttgcaa atggcagcag acccttatgg tgataggttg    720
tttttttatt tgcgaaagga acaaatgttt gctagacact ttttaatag gccggtact    780
gtggggaac ctgtgcctga tgacctgttg gtaaaggggg gtaataatag atcatctgta    840
gctagtagta tttatgtaca tacacctagt ggctcattgg tgtcttcaga ggctcaatta    900
tttaataaac catattggct tcaaaaggct cagggacata caatggtat ttgctgggga    960
aaccacttgt ttgttactgt ggtagatacc acacgcagta caaatatgac actatgtgca   1020
tctgtgtcta aatctgctac atacactaat tcagattata aggaatacat gcgccatgtg   1080
gaagagtttg atttacagtt tattttcaa ttgtgtagca ttacattatc tgcagaagtc   1140
atggcctata tacacacaat gaatccttct gttttggagg actggaactt tggtttatcg   1200
cctccaccaa atggtacact ggaggatact tatagatatg tacagtcaca ggccattacc   1260
tgtcagaaac ccacacccga aaagaaaaa caggacccct ataaggatat gagtttttgg   1320
gaggttaact taaaagaaaa gttttcttat gaattagatc agtttccccct tggacgtaag   1380
tttttattgc aaagtggata tcgaggacgg acgtctgctc gtacaggtat aaagcgccca   1440
gctgtgtcta agccctctac agcccccaaa cgaaaacgta ccaaaaccag aaagtaa      1497
```

<210> SEQ ID NO 7
<211> LENGTH: 496
<212> TYPE: PRT
<213> ORGANISM: Artificial sequence
<220> FEATURE:
<223> OTHER INFORMATION: Truncated HPV6 L1 protein

<400> SEQUENCE: 7

```
Met Asp Ser Thr Val Tyr Val Pro Pro Asn Pro Val Ser Lys Val
1               5                  10                  15

Val Ala Thr Asp Ala Tyr Val Thr Arg Thr Asn Ile Phe Tyr His Ala
            20                  25                  30

Ser Ser Ser Arg Leu Leu Ala Val Gly His Pro Tyr Phe Ser Ile Lys
        35                  40                  45

Arg Ala Asn Lys Thr Val Val Pro Lys Val Ser Gly Tyr Gln Tyr Arg
    50                  55                  60

Val Phe Lys Val Val Leu Pro Asp Pro Asn Lys Phe Ala Leu Pro Asp
65                  70                  75                  80

Ser Ser Leu Phe Asp Pro Thr Thr Gln Arg Leu Val Trp Ala Cys Thr
                85                  90                  95

Gly Leu Glu Val Gly Arg Gly Gln Pro Leu Gly Val Gly Val Ser Gly
            100                 105                 110

His Pro Phe Leu Asn Lys Tyr Asp Asp Val Glu Asn Ser Gly Ser Gly
        115                 120                 125

Gly Asn Pro Gly Gln Asp Asn Arg Val Asn Val Gly Met Asp Tyr Lys
    130                 135                 140

Gln Thr Gln Leu Cys Met Val Gly Cys Ala Pro Pro Leu Gly Glu His
145                 150                 155                 160

Trp Gly Lys Gly Lys Gln Cys Thr Asn Thr Pro Val Gln Ala Gly Asp
                165                 170                 175

Cys Pro Pro Leu Glu Leu Ile Thr Ser Val Ile Gln Asp Gly Asp Met
            180                 185                 190

Val Asp Thr Gly Phe Gly Ala Met Asn Phe Ala Asp Leu Gln Thr Asn
```

```
                195                 200                 205
Lys Ser Asp Val Pro Ile Asp Ile Cys Gly Thr Thr Cys Lys Tyr Pro
210                 215                 220

Asp Tyr Leu Gln Met Ala Ala Asp Pro Tyr Gly Asp Arg Leu Phe Phe
225                 230                 235                 240

Phe Leu Arg Lys Glu Gln Met Phe Ala Arg His Phe Asn Arg Ala
                245                 250                 255

Gly Glu Val Gly Glu Pro Val Pro Asp Thr Leu Ile Ile Lys Gly Ser
                260                 265                 270

Gly Asn Arg Thr Ser Val Gly Ser Ser Ile Tyr Val Asn Thr Pro Ser
                275                 280                 285

Gly Ser Leu Val Ser Ser Glu Ala Gln Leu Phe Asn Lys Pro Tyr Trp
                290                 295                 300

Leu Gln Lys Ala Gln Gly His Asn Asn Gly Ile Cys Trp Gly Asn Gln
305                 310                 315                 320

Leu Phe Val Thr Val Asp Thr Thr Arg Ser Thr Asn Met Thr Leu
                325                 330                 335

Cys Ala Ser Val Thr Thr Ser Ser Thr Tyr Thr Asn Ser Asp Tyr Lys
                340                 345                 350

Glu Tyr Met Arg His Val Glu Glu Tyr Asp Leu Gln Phe Ile Phe Gln
                355                 360                 365

Leu Cys Ser Ile Thr Leu Ser Ala Glu Val Val Ala Tyr Ile His Thr
370                 375                 380

Met Asn Pro Ser Val Leu Glu Asp Trp Asn Phe Gly Leu Ser Pro Pro
385                 390                 395                 400

Pro Asn Gly Thr Leu Glu Asp Thr Tyr Arg Tyr Val Gln Ser Gln Ala
                405                 410                 415

Ile Thr Cys Gln Lys Pro Thr Pro Glu Lys Gln Lys Pro Asp Pro Tyr
                420                 425                 430

Lys Asn Leu Ser Phe Trp Glu Val Asn Leu Lys Glu Lys Phe Ser Ser
                435                 440                 445

Glu Leu Asp Gln Tyr Pro Leu Gly Arg Lys Phe Leu Leu Gln Ser Gly
450                 455                 460

Tyr Arg Gly Arg Ser Ser Ile Arg Thr Gly Val Lys Arg Pro Ala Val
465                 470                 475                 480

Ser Lys Ala Ser Ala Ala Pro Lys Arg Lys Arg Ala Lys Thr Lys Arg
                485                 490                 495

<210> SEQ ID NO 8
<211> LENGTH: 502
<212> TYPE: PRT
<213> ORGANISM: Artificial sequence
<220> FEATURE:
<223> OTHER INFORMATION: Truncated HPV16 L1 protein

<400> SEQUENCE: 8

Met Leu Pro Ser Glu Ala Thr Val Tyr Leu Pro Pro Val Pro Val Ser
1               5                   10                  15

Lys Val Val Ser Thr Asp Glu Tyr Val Ala Arg Thr Asn Ile Tyr Tyr
                20                  25                  30

His Ala Gly Thr Ser Arg Leu Leu Ala Val Gly His Pro Tyr Phe Pro
                35                  40                  45

Ile Lys Lys Pro Asn Asn Asn Lys Ile Leu Val Pro Lys Val Ser Gly
                50                  55                  60

Leu Gln Tyr Arg Val Phe Arg Ile His Leu Pro Asp Pro Asn Lys Phe
```

```
            65                  70                  75                  80

Gly Phe Pro Asp Thr Ser Phe Tyr Asn Pro Asp Thr Gln Arg Leu Val
                    85                  90                  95

Trp Ala Cys Val Gly Val Glu Val Gly Arg Gly Gln Pro Leu Gly Val
                100                 105                 110

Gly Ile Ser Gly His Pro Leu Leu Asn Lys Leu Asp Asp Thr Glu Asn
                115                 120                 125

Ala Ser Ala Tyr Ala Ala Asn Ala Gly Val Asp Asn Arg Glu Cys Ile
            130                 135                 140

Ser Met Asp Tyr Lys Gln Thr Gln Leu Cys Leu Ile Gly Cys Lys Pro
145                 150                 155                 160

Pro Ile Gly Glu His Trp Gly Lys Gly Ser Pro Cys Thr Asn Val Ala
                165                 170                 175

Val Asn Pro Gly Asp Cys Pro Pro Leu Glu Leu Ile Asn Thr Val Ile
                180                 185                 190

Gln Asp Gly Asp Met Val Asp Thr Gly Phe Gly Ala Met Asp Phe Thr
            195                 200                 205

Thr Leu Gln Ala Asn Lys Ser Glu Val Pro Leu Asp Ile Cys Thr Ser
210                 215                 220

Ile Cys Lys Tyr Pro Asp Tyr Ile Lys Met Val Ser Glu Pro Tyr Gly
225                 230                 235                 240

Asp Ser Leu Phe Phe Tyr Leu Arg Arg Glu Gln Met Phe Val Arg His
                245                 250                 255

Leu Phe Asn Arg Ala Gly Ala Val Gly Asp Asn Val Pro Asp Asp Leu
                260                 265                 270

Tyr Ile Lys Gly Ser Gly Ser Thr Ala Asn Leu Ala Ser Ser Asn Tyr
            275                 280                 285

Phe Pro Thr Pro Ser Gly Ser Met Val Thr Ser Asp Ala Gln Ile Phe
            290                 295                 300

Asn Lys Pro Tyr Trp Leu Gln Arg Ala Gln Gly His Asn Asn Gly Ile
305                 310                 315                 320

Cys Trp Gly Asn Gln Leu Phe Val Thr Val Val Asp Thr Thr Arg Ser
                325                 330                 335

Thr Asn Met Ser Leu Cys Ala Ala Ile Ser Thr Ser Glu Thr Thr Tyr
                340                 345                 350

Lys Asn Thr Asn Phe Lys Glu Tyr Leu Arg His Gly Glu Glu Tyr Asp
            355                 360                 365

Leu Gln Phe Ile Phe Gln Leu Cys Lys Ile Thr Leu Thr Ala Asp Ile
370                 375                 380

Met Thr Tyr Ile His Ser Met Asn Ser Thr Ile Leu Glu Asp Trp Asn
385                 390                 395                 400

Phe Gly Leu Gln Pro Pro Gly Gly Thr Leu Glu Asp Thr Tyr Arg
                405                 410                 415

Phe Val Thr Ser Gln Ala Ile Ala Cys Gln Lys His Thr Pro Pro Ala
                420                 425                 430

Pro Lys Glu Asp Pro Leu Lys Lys Tyr Thr Phe Trp Glu Val Asn Leu
            435                 440                 445

Lys Glu Lys Phe Ser Ala Asp Leu Asp Gln Phe Pro Leu Gly Arg Lys
450                 455                 460

Phe Leu Leu Gln Ala Gly Leu Glu Ala Lys Pro Lys Phe Thr Leu Gly
465                 470                 475                 480

Lys Arg Lys Ala Thr Pro Thr Thr Ser Ser Thr Ser Thr Thr Ala Lys
                485                 490                 495
```

Arg Lys Lys Arg Lys Leu
            500

<210> SEQ ID NO 9
<211> LENGTH: 504
<212> TYPE: PRT
<213> ORGANISM: Artificial sequence
<220> FEATURE:
<223> OTHER INFORMATION: Truncated HPV18 L1 protein

<400> SEQUENCE: 9

Met Arg Pro Ser Asp Asn Thr Val Tyr Leu Pro Pro Ser Val Ala
1               5                   10                  15

Arg Val Val Asn Thr Asp Asp Tyr Val Thr Arg Thr Ser Ile Phe Tyr
                20                  25                  30

His Ala Gly Ser Ser Arg Leu Leu Thr Val Gly Asn Pro Tyr Phe Arg
                35                  40                  45

Val Pro Ala Gly Gly Gly Asn Lys Gln Asp Ile Pro Lys Val Ser Ala
            50                  55                  60

Tyr Gln Tyr Arg Val Phe Arg Val Gln Leu Pro Asp Pro Asn Lys Phe
65              70                  75                  80

Gly Leu Pro Asp Thr Ser Ile Tyr Asn Pro Glu Thr Gln Arg Leu Val
                85                  90                  95

Trp Ala Cys Ala Gly Val Glu Ile Gly Arg Gly Gln Pro Leu Gly Val
                100                 105                 110

Gly Leu Ser Gly His Pro Phe Tyr Asn Lys Leu Asp Asp Thr Glu Ser
            115                 120                 125

Ser His Ala Ala Thr Ser Asn Val Ser Glu Asp Val Arg Asp Asn Val
            130                 135                 140

Ser Val Asp Tyr Lys Gln Thr Gln Leu Cys Ile Leu Gly Cys Ala Pro
145             150                 155                 160

Ala Ile Gly Glu His Trp Ala Lys Gly Thr Ala Cys Lys Ser Arg Pro
                165                 170                 175

Leu Ser Gln Gly Asp Cys Pro Pro Leu Glu Leu Lys Asn Thr Val Leu
                180                 185                 190

Glu Asp Gly Asp Met Val Asp Thr Gly Tyr Gly Ala Met Asp Phe Ser
            195                 200                 205

Thr Leu Gln Asp Thr Lys Cys Glu Val Pro Leu Asp Ile Cys Gln Ser
            210                 215                 220

Ile Cys Lys Tyr Pro Asp Tyr Leu Gln Met Ser Ala Asp Pro Tyr Gly
225             230                 235                 240

Asp Ser Met Phe Phe Cys Leu Arg Arg Glu Gln Leu Phe Ala Arg His
                245                 250                 255

Phe Trp Asn Arg Ala Gly Thr Met Gly Asp Thr Val Pro Gln Ser Leu
                260                 265                 270

Tyr Ile Lys Gly Thr Gly Met Arg Ala Ser Pro Gly Ser Cys Val Tyr
            275                 280                 285

Ser Pro Ser Pro Ser Gly Ser Ile Val Thr Ser Asp Ser Gln Leu Phe
            290                 295                 300

Asn Lys Pro Tyr Trp Leu His Lys Ala Gln Gly His Asn Asn Gly Val
305             310                 315                 320

Cys Trp His Asn Gln Leu Phe Val Thr Val Val Asp Thr Thr Arg Ser
                325                 330                 335

Thr Asn Leu Thr Ile Cys Ala Ser Thr Gln Ser Pro Val Pro Gly Gln
                340                 345                 350

```
Tyr Asp Ala Thr Lys Phe Lys Gln Tyr Ser Arg His Val Glu Glu Tyr
            355                 360                 365

Asp Leu Gln Phe Ile Phe Gln Leu Cys Thr Ile Thr Leu Thr Ala Asp
    370                 375                 380

Val Met Ser Tyr Ile His Ser Met Asn Ser Ser Ile Leu Glu Asp Trp
385                 390                 395                 400

Asn Phe Gly Val Pro Pro Pro Thr Thr Ser Leu Val Asp Thr Tyr
                405             410                 415

Arg Phe Val Gln Ser Val Ala Ile Ala Cys Gln Lys Asp Ala Ala Pro
            420             425                 430

Ala Glu Asn Lys Asp Pro Tyr Asp Lys Leu Lys Phe Trp Asn Val Asp
            435                 440                 445

Leu Lys Glu Lys Phe Ser Leu Asp Leu Asp Gln Tyr Pro Leu Gly Arg
    450                 455                 460

Lys Phe Leu Val Gln Ala Gly Leu Arg Arg Lys Pro Thr Ile Gly Pro
465                 470                 475                 480

Arg Lys Arg Ser Ala Pro Ser Ala Thr Thr Ala Ser Lys Pro Ala Lys
                485                 490                 495

Arg Val Arg Val Arg Ala Arg Lys
                500

<210> SEQ ID NO 10
<211> LENGTH: 27
<212> TYPE: DNA
<213> ORGANISM: Artificial sequence
<220> FEATURE:
<223> OTHER INFORMATION: primer

<400> SEQUENCE: 10
catatgagcg acagcacagt atatgtg                                        27

<210> SEQ ID NO 11
<211> LENGTH: 30
<212> TYPE: DNA
<213> ORGANISM: Artificial sequence
<220> FEATURE:
<223> OTHER INFORMATION: primer

<400> SEQUENCE: 11
gtcgacttac tttctggttt tggtacgttt                                     30
```